(12) United States Patent
Chang et al.

(10) Patent No.: US 9,910,190 B2
(45) Date of Patent: Mar. 6, 2018

(54) POLY(OXAZOLINE-CO-ETHYLENEIMINE)-EPICHLOROHYDRIN COPOLYMERS AND USES THEREOF

(71) Applicant: Novartis AG, Basel (CH)

(72) Inventors: Frank Chang, Cumming, GA (US); Troy Vernon Holland, Suwanee, GA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/633,999

(22) Filed: Jun. 27, 2017

(65) Prior Publication Data

US 2017/0293050 A1  Oct. 12, 2017

Related U.S. Application Data

(62) Division of application No. 14/833,477, filed on Aug. 24, 2015.

(60) Provisional application No. 62/041,762, filed on Aug. 26, 2014.

(51) Int. Cl.

| | |
|---|---|
| G02B 1/10 | (2015.01) |
| C07D 205/04 | (2006.01) |
| G02B 1/04 | (2006.01) |
| G02C 7/04 | (2006.01) |
| C08G 73/02 | (2006.01) |
| C08J 3/24 | (2006.01) |
| C08G 73/06 | (2006.01) |
| C09D 179/02 | (2006.01) |
| C09D 5/00 | (2006.01) |

(52) U.S. Cl.
CPC ......... *G02B 1/043* (2013.01); *C08G 73/0226* (2013.01); *C08G 73/0233* (2013.01); *C08G 73/06* (2013.01); *C08J 3/247* (2013.01); *C09D 5/00* (2013.01); *C09D 179/02* (2013.01); *G02C 7/049* (2013.01); *C08J 2379/02* (2013.01); *G02C 2202/16* (2013.01)

(58) Field of Classification Search
None
See application file for complete search history.

(56) References Cited

U.S. PATENT DOCUMENTS

| | | | | |
|---|---|---|---|---|
| 3,640,909 A * | 2/1972 | Jones et al. | .......... | C08G 3/0233 162/164.3 |
| 5,773,527 A * | 6/1998 | Tomalia | ........... | A61K 47/48961 525/374 |
| 6,974,856 B1 * | 12/2005 | Kataoka | ........... | C08G 65/33317 525/412 |
| 2011/0134387 A1* | 6/2011 | Samuel | .................. | G02B 1/043 351/159.33 |

OTHER PUBLICATIONS

Linear polyethyleneimine produced by partial acid hydrolysis of poly(2-ethyl-2-oxazoline) for DNA and siRNA delivery in vitro, Fernandes et al., International Journal of Nanamedicine, 2013:8 4091-4102.*

* cited by examiner

*Primary Examiner* — Peter A Salamon
(74) *Attorney, Agent, or Firm* — Jian Zhou

(57) ABSTRACT

The invention is related to poly(2-oxazoline-co-ethyleneimine)-epichlorohydrin copolymers and chemically-modified derivatives thereof as well as their uses in formation of non-silicone hydrogel coatings on silicone hydrogel contact lenses.

14 Claims, No Drawings

US 9,910,190 B2

POLY(OXAZOLINE-CO-ETHYLENEIMINE)-EPICHLOROHYDRIN COPOLYMERS AND USES THEREOF

This application claims the benefits under 35 USC § 119 (e) of U.S. provisional application No. 62/041,762 filed 26 Aug. 2014, incorporated by reference in its entirety.

The present invention generally relates to poly(2-oxazoline-co-ethylenimine)-epichlorohydrin copolymers and chemically-modified derivatives thereof suitable for applying a hydrogel coating onto a silicone hydrogel contact lens in a cost-effective and time-efficient manner. In addition, the present invention provides an ophthalmic lens product.

BACKGROUND

Soft silicone hydrogel contact lenses are increasingly becoming popular because of their high oxygen permeability and comfort. But, a silicone hydrogel material typically has a surface, or at least some areas of its surface, which is hydrophobic (non-wettable) and susceptible to adsorbing lipids or proteins from the ocular environment and may adhere to the eye. Thus, a silicone hydrogel contact lens will generally require a surface modification.

A known approach for modifying the hydrophilicity of a relatively hydrophobic contact lens material is through the use of a plasma treatment, for example, commercial lenses such as Focus NIGHT & DAY™ and O2OPTIX™ (CIBA VISION), and PUREVISION™ (Bausch & Lomb) utilize this approach in their production processes. Advantages of a plasma coating, such as, e.g., those may be found with Focus NIGHT & DAY™, are its durability, relatively high hydrophilicity/wettability), and low susceptibility to lipid and protein deposition and adsorption. But, plasma treatment of silicone hydrogel contact lenses may not be cost effective, because the preformed contact lenses must typically be dried before plasma treatment and because of relative high capital investment associated with plasma treatment equipment.

Various other approaches are proposed and/or used for modifying the surface hydrophilicity of a silicone hydrogel contact lens. Examples of such other approaches include incorporation of wetting agents (hydrophilic polymers) into a lens formulation for making the silicone hydrogel contact lens (see, e.g., U.S. Pat. Nos. 6,367,929, 6,822,016, 7,052, 131, and 7,249,848); a layer-by-layer (LbL) polyionic material deposition technique (see, e.g., U.S. Pat. Nos. 6,451,871; 6,719,929; 6,793,973; 6,884,457; 6,896,926; 6,926,965; 6,940,580; and 7,297,725, and U.S. Pat. Appl. Pub. Nos. 2007/0229758A1; 2008/0174035A1 and 2008/0152800A1); crosslinking of LbL coatings on contact lenses has been proposed in commonly-owned copending US pat. Appl. pub. Nos. 2008/0226922 A1 and 2009/0186229 A1; and attachment of hydrophilic polymers onto contact lenses according to various mechanisms (see for example, U.S. Pat. Nos. 6,099,122, 6,436,481, 6,440,571, 6,447,920, 6,465,056, 6,521,352, 6,586,038, 6,623,747, 6,730,366, 6,734,321, 6,835,410, 6,878,399, 6,923,978, 6,440,571, and 6,500,481, US Pat. Appl. Pub. Nos. 2009/0145086 A1, 2009/0145091A1, 2008/0142038A1, and 2007/0122540A1). Although those techniques can be used in rendering a silicone hydrogel material wettable, there are some shortcomings in those techniques. For example, wetting agents may impart haziness to the resultant lenses because of their incompatibility with other silicone components in the lens formulation and may not provide a durable hydrophilic surface for extended wear purposes. LbL coatings may not be as durable as plasma coatings and may have relatively high densities of surface charges; which may interfere with contact lens cleaning and disinfecting solutions. Crosslinked LbL coatings may have a hydrophilicity and/or wettability inferior than original LbL coatings (prior to crosslinking) and still have relative high densities of surface charges. In addition, they may not be cost-effective and/or time-efficient for implementation in a mass production environment, because they typically require relatively long time and/or involve laborious, multiple steps to obtain a hydrophilic coating.

Recently, a new cost-effective approach has been described in U.S. Pat. No. 8,529,057 (herein incorporated by reference in its entirety) for applying a non-silicone hydrogel coating onto a silicone hydrogel contact lens. It discloses that a partially-crosslinked hydrophilic polymeric material derived from a polyamidoamine epichlorohydrin (PAE) and a wetting agent are used in the formation of non-silicone hydrogel coating on a contact lens. Although this new approach can provide silicone hydrogel contact lenses with durable hydrophilic coatings thereon, its applicability and advantages can be limited by the lack of versatility and controllability in the levels of hydrophilicity and/or reactive functional group contents of the partially-crosslinked hydrophilic polymeric material.

Therefore, there is still a need for reactive copolymers having desired level of hydrophilicity and/or functional groups content for applying a non-silicone hydrogel coating onto a silicone hydrogel contact lens.

SUMMARY OF THE INVENTION

The invention, in one aspect, provides a poly(2-oxazoline-co-ethyleneimine)-epichlorohydrin copolymer comprising: from about 2% to about 95% by mole of N-acyl-iminoethylene monomeric units; from about 0.5% to about 95% by mole of azetidinium monomeric units; from 0 to about 60% by mole of ethylenimine monomeric units; and from 0 to about 5% by mole of crosslinking units, relative to the total composition of the poly(2-oxazoline-co-ethyleneimine)-epichlorohydrin copolymer.

The invention, in another aspect, provides a water-soluble and thermally-crosslinkable hydrophilic polymeric material which comprises: azetidinium groups; from about 20% to about 95% by weight of first polymer chains derived from a poly(2-oxazoline-co-ethyleneimine)-epichlorohydrin copolymer of the invention; and from about 5% to about 80% by weight of hydrophilic moieties or second polymer chains derived from at least one hydrophilicity-enhancing agent having at least one reactive functional group selected from the group consisting of primary amino group, secondary amino group, carboxyl group, thiol group, and combination thereof.

The invention, in a further aspect, provides methods for producing coated silicone hydrogel contact lenses each having a crosslinked hydrophilic coating thereon, involving use of at least a poly(2-oxazoline-co-ethyleneimine)-epichlorohydrin copolymer of the invention fully described above and/or at least one water-soluble and thermally crosslinkable hydrophilic polymeric material of the invention fully described above.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

"About" as used herein means that a number referred to as "about" comprises the recited number plus or minus 1-10% of that recited number.

An "ophthalmic device", as used herein, refers to a contact lens (hard or soft), an intraocular lens, a corneal onlay, other ophthalmic devices (e.g., stents, glaucoma shunt, or the like) used on or about the eye or ocular vicinity.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens (e.g., hydrogel lens or silicone hydrogel lens), a hard lens, or a hybrid lens. A "silicone hydrogel contact lens" refers to a contact lens comprising a silicone hydrogel bulk (core) material.

A "hydrogel" or "hydrogel material" refers to a cross-linked polymeric material which is insoluble in water, but can absorb at least 10 percent by weight of water when it is fully hydrated.

A "silicone hydrogel" refers to a silicone-containing hydrogel obtained by copolymerization of a polymerizable composition comprising at least one silicone-containing monomer or at least one silicone-containing macromer or at least one crosslinkable silicone-containing prepolymer.

As used in this application, the term "non-silicone hydrogel" refers to a hydrogel that is theoretically free of silicon.

"Hydrophilic," as used herein, describes a material or portion thereof that will more readily associate with water than with lipids.

A "vinylic monomer" refers to a compound that has one sole ethylenically unsaturated group, is soluble in a solvent, and can be polymerized actinically or thermally.

The term "soluble", in reference to a compound or material in a solvent, means that the compound or material can be dissolved in the solvent to give a solution with a concentration of at least about 0.5% by weight at room temperature (i.e., a temperature of about 22° C. to about 28° C.).

The term "insoluble", in reference to a compound or material in a solvent, means that the compound or material can be dissolved in the solvent to give a solution with a concentration of less than 0.005% by weight at room temperature (as defined above).

As used in this application, the term "ethylenically unsaturated group" is employed herein in a broad sense and is intended to encompass any groups containing at least one >C=C< group. Exemplary ethylenically unsaturated groups include without limitation (meth)acryloyl

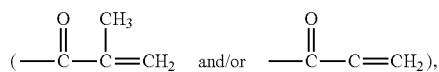

allyl, vinyl, styrenyl, or other C=C containing groups.

The term "(meth)acrylamide" refers to methacrylamide and/or acrylamide.

The term "(meth)acrylate" refers to methacrylate and/or acrylate.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV/visible irradiation, ionizing radiation (e.g. gamma ray or X-ray irradiation), microwave irradiation, and the like. Thermal curing or actinic curing methods are well-known to a person skilled in the art.

A "hydrophilic vinylic monomer", as used herein, refers to a vinylic monomer which as a homopolymer typically yields a polymer that is water-soluble or can absorb at least 10 percent by weight of water.

A "hydrophobic vinylic monomer", as used herein, refers to a vinylic monomer which as a homopolymer typically yields a polymer that is insoluble in water and can absorb less than 10 percent by weight of water.

A "macromer" or "prepolymer" refers to a compound or polymer that contains ethylenically unsaturated groups and has an average molecular weight of greater than 700 Daltons.

As used in this application, the term "vinylic crosslinker" refers to a compound having at least two ethylenically unsaturated groups. A "vinylic crosslinking agent" refers to a vinylic crosslinker having a molecular weight of 700 Daltons or less.

As used in this application, the term "polymer" means a material formed by polymerizing/crosslinking one or more monomers or macromers or prepolymers or combinations thereof.

As used in this application, the term "molecular weight" of a polymeric material (including monomeric or macromeric materials) refers to the weight-average molecular weight unless otherwise specifically noted or unless testing conditions indicate otherwise.

A "polysiloxane" refers to a compound containing a polysiloxane segment of

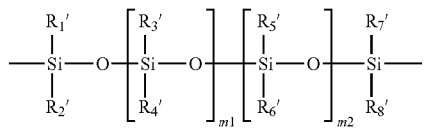

in which m1 and m2 independently of each other are an integer of from 0 to 500 and (m1+m2) is from 2 to 500, $R_1'$, $R_2'$, $R_3'$, $R_4'$, $R_5'$, $R_6'$, $R_7'$, and $R_8'$ independently of one another, are $C_1$-$C_{10}$ alkyl, $C_1$-$C_4$ alkyl- or $C_1$-$C_4$-alkoxy-substituted phenyl, $C_1$-$C_{10}$ fluoroalkyl, $C_1$-$C_{10}$ fluoroether, $C_6$-$C_{18}$ aryl radical, -alk-$(OC_2H_4)_{m3}$—OR' (in which alk is $C_1$-$C_6$ alkyl diradical, R' is H or $C_1$-$C_4$ alkyl and m3 is an integer from 1 to 10), or a linear hydrophilic polymer chain.

A "polycarbosiloxane" refers to a compound containing a polycarbosiloxane segment of

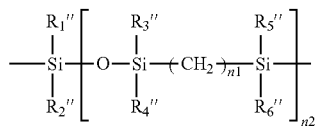

in which n1 is an integer of 2 or 3, n2 is an integer of from 2 to 100 (preferably from 2 to 20, more preferably from 2 to 10, even more preferably from 2 to 6), $R_1''$, $R_2''$, $R_3''$, $R_4''$, $R_5''$, and $R_6''$ independent of one another are a $C_1$-$C_6$ alkyl radical (preferably methyl).

The term "fluid" as used herein indicates that a material is capable of flowing like a liquid.

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkyl triradical" refers to a trivalent radical obtained by removing two hydrogen atoms from an alkyl. An alkyl triradical forms three bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), $C_1$-$C_4$ alkyl, $C_1$-$C_4$ alkoxy, $C_1$-$C_4$ alkylthio (alkyl sulfide), $C_1$-$C_4$ acylamino, $C_1$-$C_4$ alkylamino, di-$C_1$-$C_4$ alkylamino, halogen atom (Br or Cl), and combinations thereof.

In this application, an "oxazoline" refers to a compound of

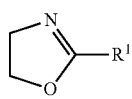

in which $R^1$ is hydrogen, $C_1$-$C_{18}$ alkyl, $C_1$-$C_4$ alkyl-substituted phenyl, $C_1$-$C_4$-alkoxy-substituted phenyl, $C_6$-$C_{18}$ aryl radical, N-pyrrolidonyl-$C_1$-$C_4$ alkyl, a monovalent radical of -alk-(OC$_2$H$_4$)$_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)), preferably $R^1$ is methyl, ethyl, propyl, N-pyrrolidonyl-$C_1$-$C_4$ alkyl, a monovalent radical of -alk-(OC$_2$H$_4$)$_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)).

In this application, the term "polyoxazoline" refers to a linear polymer which is obtained in a ring-opening polymerization of one or more oxazolines and generally has a formula of

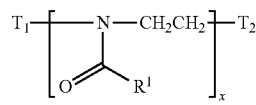

in which: T1 and T2 are two terminal groups; $R^1$ is hydrogen, $C_1$-$C_8$ alkyl, $C_1$-$C_4$ alkyl-substituted phenyl, $C_1$-$C_4$-alkoxy-substituted phenyl, $C_6$-$C_{18}$ aryl radical, N-pyrrolidonyl-$C_1$-$C_4$ alkyl, a monovalent radical of -alk-(OC$_2$H$_4$)$_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)), preferably R1 is methyl, ethyl, propyl, N-pyrrolidonyl-$C_1$-$C_4$ alkyl, a monovalent radical of -alk-(OC$_2$H$_4$)$_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)); x is an integer from 5 to 500. A polyoxazoline segment has a divalent polymer chain of a formula of

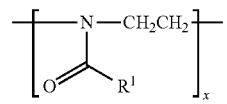

in which $R^1$ and x are as defined above.

In this application, the term "poly(2-oxazoline-co-ethyleneimine)" refers to a statistical copolymer having a formula of

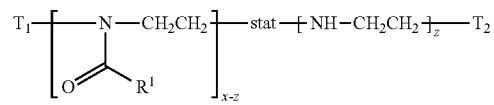

in which: T1 and T2 are terminal groups; $R^1$ is hydrogen, $C_1$-$C_{18}$ alkyl, $C_1$-$C_4$ alkyl-substituted phenyl, $C_1$-$C_4$-alkoxy-substituted phenyl, $C_6$-$C_{18}$ aryl radical, N-pyrrolidonyl-$C_1$-$C_4$ alkyl, a monovalent radical of -alk-(OC$_2$H$_4$)$_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)), preferably R1 is methyl, ethyl, propyl, N-pyrrolidonyl-$C_1$-$C_4$ alkyl, a monovalent radical of -alk-(OC$_2$H$_4$)$_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)); x is an integer from 5 to 500; z is an integer equal to or less than x. A poly(2-oxazoline-co-ethyleneimine) is obtained by hydrolyzing a polyoxazoline.

In this application, the term "poly(2-oxazoline-co-ethyleneimine)-epichlorohydrin" refers to a polymer obtained by reacting a poly(2-oxazoline-co-ethyleneimine) with epichlorohydrin to convert all or substantial percentage (≥90%) of the secondary amine groups of the poly(2-oxazoline-co-ethyleneimine) into azetidinium groups.

In this application the term "azetidinium" or "3-hydroxyazetidinium" refers to a positively-charged, divalent radical (or group or moiety) of

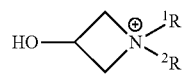

in which $^1$R and $^2$R are a hydrocarbon group.

The term "azlactone" refers to a mono-valent radical of formula

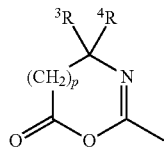

in which p is 0 or 1; $^3R$ and $^4R$ independently of each other is $C_1$-$C_8$ alkyl (preferably methyl).

As used in this application, the term "phosphorylcholine" refers to a monovalent zwitterionic group of

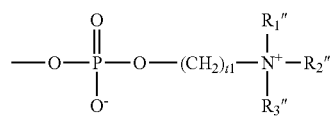

in which t1 is an integer of 1 to 5 and $R_1''$, $R_2''$ and $R_3''$ independently of one another are $C_1$-$C_8$ alkyl or $C_1$-$C_8$ hydroxyalkyl.

As used in this application, the term "reactive vinylic monomer" refers to any vinylic monomer having at least one reactive functional group selected from the group consisting of carboxyl group, primary amino group, and secondary amino group.

As used in this application, the term "non-reactive vinylic monomer" refers to any vinylic monomer (either hydrophilic or hydrophobic vinylic monomer) free of carboxyl group, primary amino group, secondary amino group, epoxide group, isocyanate group, azlactone group, or aziridine group. A non-reactive vinylic monomer can include a hydroxyl group or a tertiary or quaternium amino group.

A free radical initiator can be either a photoinitiator or a thermal initiator. A "photoinitiator" refers to a chemical that initiates free radical crosslinking/polymerizing reaction by the use of light. A "thermal initiator" refers to a chemical that initiates radical crosslinking/polymerizing reaction by the use of heat energy.

A "water contact angle" refers to an average water contact angle (i.e., contact angles measured by Sessile Drop method) at the room temperature, which is obtained by averaging measurements of contact angles with at least 3 individual contact lenses.

The term "intactness" in reference to a coating on a silicone hydrogel contact lens is intended to describe the extent to which the contact lens can be stained by Sudan Black in a Sudan Black staining test described in Example 1. Good intactness of the coating on a silicone hydrogel contact lens means that there is practically no Sudan Black staining of the contact lens.

The term "durability" in reference to a coating on a silicone hydrogel contact lens is intended to describe that the coating on the silicone hydrogel contact lens can survive a digital rubbing test.

As used herein, "surviving a digital rubbing test" or "surviving a durability test" in reference to a coating on a contact lens means that after digitally rubbing the lens according to a procedure described in Example 1, water contact angle on the digitally rubbed lens is still about 100 degrees or less, preferably about 90 degrees or less, more preferably about 80 degrees or less, most preferably about 70 degrees or less.

"Ophthalmically compatible", as used herein, refers to a material or surface of a material which may be in intimate contact with the ocular environment for an extended period of time without significantly damaging the ocular environment and without significant user discomfort.

The term "ophthalmically safe" with respect to a packaging solution for sterilizing and storing contact lenses is meant that a contact lens stored in the solution is safe for direct placement on the eye without rinsing after autoclave and that the solution is safe and sufficiently comfortable for daily contact with the eye via a contact lens. An ophthalmically-safe packaging solution after autoclave has a tonicity and a pH that are compatible with the eye and is substantially free of ocularly irritating or ocularly cytotoxic materials according to international ISO standards and U.S. FDA regulations.

The term "modulus" or "elastic modulus" in reference to a contact lens or a material means the tensile modulus or Young's modulus which is a measure of the stiffness of a contact lens or a material. The modulus can be measured using a method in accordance with ANSI Z80.20 standard. A person skilled in the art knows well how to determine the elastic modulus of a silicone hydrogel material or a contact lens. For example, all commercial contact lenses have reported values of elastic modulus.

An "organic-based solution" refers to a solution which is a homogeneous mixture consisting of an organic-based solvent and one or more solutes dissolved in the organic based solvent. An organic-based coating solution refers to an organic-based solution containing at least one polymeric coating material as a solute in the solution.

An "organic-based solvent" is intended to describe a solvent system which consists of one or more organic solvents and optionally about 40% or less, preferably about 30% or less, more preferably about 20% or less, even more preferably about 10% or less, in particular about 5% or less by weight of water relative to the weight of the solvent system.

The invention is generally related to poly(2-oxazoline-co-ethyleneimine)-epichlorohydrin copolymers (i.e., a reaction product of poly(2-oxazoline-co-ethyleneimine) copolymers and epichlorohydrin) and chemically-modified derivatives thereof as well as their uses in forming a non-silicone hydrogel coating on a contact lens (preferably a silicone hydrogel (SiHy) contact lens). A poly(2-oxazoline-co-ethyleneimine)-epichlorohydrin copolymer of the invention can be tailored to have desired degrees of hydrophilicity and reactivity by adjusting the amount of amide, amine, and azetidinium groups. Such azetidinium-containing copolymers can be used as an anchoring polymer and/or a water-soluble and thermally-reactive hydrophilic polymeric material for forming a hydrogel coating, according to thermally-induced reaction mechanism involving an azetidnium group and a carboxyl, primary amino or secondary amino group as shown below:

Scheme I

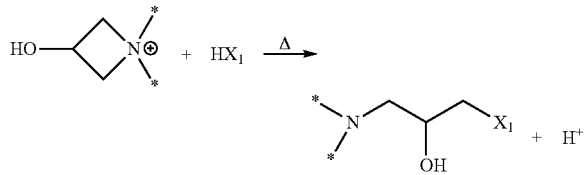

in which $X_1$ is —S—*, —OC(=O)—*, or —NR'—* in which R' is hydrogen, a $C_1$-$C_{20}$ unsubstituted or substituted, linear or branched alkyl group; * represents an organic radical. Such a reaction can be carried out conveniently and directly in a lens package during autoclave (i.e., heating the lens package with the lens in a packaging solution about 118° C. to about 125° C. for approximately 20-40 minutes under pressure) which is a commonly-used sterilization process in the contact lens industry. Any azetidinium groups which are not reacted with carboxyl, primary amino or secondary amino groups will be hydrolyzed during autoclave as shown below Scheme II

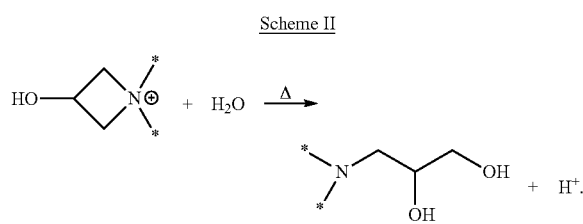

The invention, in one aspect, provides a poly(2-oxazoline-co-ethyleneimine)-epichlorohydrin copolymer (or a copolymer), which comprises, consists essential of, or consists of:
(1) N-acyl-iminoethylene monomeric units in an amount (designated as M1) of from about 2% to about 95% by mole, wherein the N-acyl-iminoethylene monomeric units have a formula of

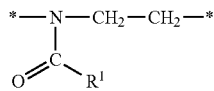

in which $R^1$ is (a) a monovalent radical $R^{1a}$ which is hydrogen, methyl, ethyl, propyl, isopropyl, N-pyrrolidonyl-$C_1$-$C_4$ alkyl, or a monovalent radical of -alk-(OC$_2$H$_4$)$_{m3}$—OR'' (in which alk is $C_1$-$C_6$ alkyl diradical, R'' is $C_1$-$C_4$ alkyl, preferably methyl, and m3 is an integer from 1 to 10 (preferably 1 to 5)), or (b) a monovalent radical $R^{1b}$ which is $C_4$-$C_{18}$ alkyl, $C_1$-$C_4$ alkyl-substituted phenyl, $C_1$-$C_4$-alkoxy-substituted phenyl, or $C_6$-$C_{18}$ aryl radical;
(2) azetidinium monomeric units in an amount (designated as M2) of from about 0.5% to about 95% by mole, wherein the azetidinium monomeric units have a formula of

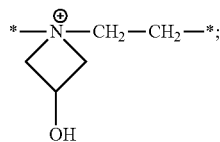

(3) ethyleneimine monomeric units in an amount (designated as M3) of from 0 to about 60% by mole, wherein the ethyleneimine monomeric units have a formula of *—NH—CH$_2$—CH$_2$—*; and
(4) crosslink units in an amount (designated as M4) of from 0 to about 5% by mole, wherein the crosslink units have a formula of

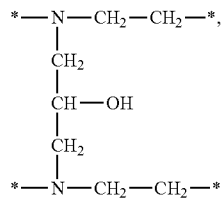

provided that (M1+M2+M3+M4) is about 100%. It should be understood that a poly(2-oxazoline-co-ethyleneimine)-epichlorohydrin copolymer of the invention can comprise two terminal groups which are not counted in the calculation of the amounts of the units in the copolymer.

A poly(2-oxazoline-co-ethyleneimine)-epichlorohydrin copolymer of the invention can be prepared from a poly(2-oxazoline) polymer (i.e., a poly(N-acyl-iminoethylene) which is obtained by polymerization of oxazoline) according to a two-step process. In the first step, a poly(2-oxazoline) polymer is partially hydrolyzed under acidic conditions to form a poly(2-oxazoline-co-ethyleneimine) copolymer. In the second step, the resultant poly(2-oxazoline-co-ethyleneimine) copolymer can react with epichlorohydrin

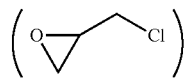

in an amount sufficient to convert all or a percentage of ethyleneimine monomeric units of the poly(2-oxazoline-co-ethyleneimine) copolymer into azetidinium monomeric units, thereby forming a poly(2-oxazoline-co-ethyleneimine)-epichlorohydrin copolymer of the invention. Where only a percentage of ethyleneimine monomeric units are converted into azetidinium monomeric units, inter- and/or intra-crosslinks may be formed as results of reactions between one azetidinium monomeric unit and one ethyleneimine monomeric unit within one single copolymer molecule or between two copolymer molecules as shown below.

Scheme III

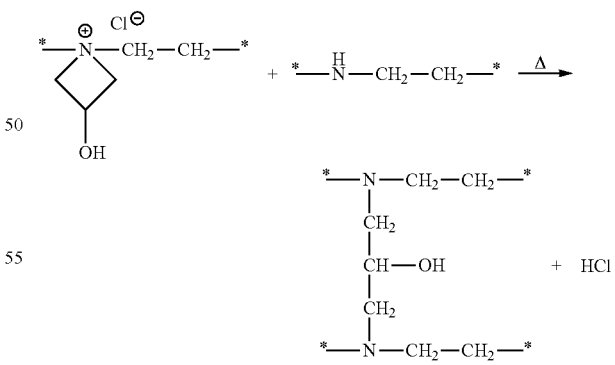

Partial hydrolysis of a poly(2-oxazoline) can be carried out according to commonly used hydrolysis methods, for examples, such as, those disclosed by De la Rosa and co-workers in Polymer Chemistry, 2014, DOI; by Jeong and coworker in *J. of Controlled Release* 2001, 73, 391-399; or by Fernandes and coworkers in *International Journal of Nanomedicine* 2013, 13(8), 4091-4102 (all of which are incorporated by reference in their entireties). As taught by De la Rosa and coworker in their paper, control over the desired degree of hydrolysis of poly(2-oxazoline) can be achieved by selecting the appropriate HCl concentration.

The secondary amine groups of one or more ethyleneimine monomeric units of the resultant poly(2-oxazoline-co-ethyleneimine) copolymer can be converted into azetidinium groups by a reaction with epichlorohydrin, under conditions well known to a person skilled in the art, for example, those disclosed by Chattopadhyay, Keul and Moeller in Macromolecular Chemistry and Physics 2012, 213, 500-512; by Obokata, Yanagisawa and Isogai in *J. Applied Polym. Sci.* 2005, 97, 2249-2255, both of which are incorporated by reference in their entireties).

Poly(2-methyl-oxazoline), poly(2-ethyl-oxazoline), poly (2-propyl-oxazoline) polymers with various molecular weights are commercially available. Other poly(2-oxazoline) can be prepared from one or more 2-oxazoline monomers according to cationic ring opening polymerization (CROP) using a microwave synthesizer (see, T. X. Viegas et al., *Bioconjugate Chemistry*, 2011, 22, 976-986; R. Hoogenboom et al., *Journal of Combinatorial Chemistry*, 2004, 7, 10-13; F. Wiesbrock et al., *Macromolecules*, 2005, 38, 5025-5034). Block poly(2-oxazoline) copolymers can be prepared from two or more different 2-oxazoline monomers by sequential one-pot monomer addition.

2-oxazoline monomer can be prepared from their corresponding nitriles according to the procedures disclosed in the published articles, such as, H. White, W. Seeliger, *Liebigs Ann. Chem.* 1974, 996; W. Seeliger, E. Aufderhaar, W. Diepers, R. Feinauer, R. Nehring, W. Thier, Hellman, *Angew. Chem.* 1966, 20, 913; and K. Lütke, R. Jordan, P. Hommes, O. Nuyken, C. Naumann, *Macromol. Biosci.* 2005, 5, 384-393 (herein incorporated by references in their entireties). For example, a 2-oxazoline of formula

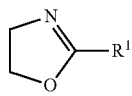

in which $R^1$ is N-pyrrolidonylethyl

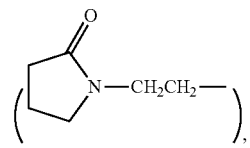

3-methoxyethyleneglycol-propyl $(CH_3—OCH_2CH_2O—C_3H_6—)$, or 3-methoxytriethyleneglycol-propyl $[CH_3—O—(CH_2CH_2O)_3—C_3H_6—]$ can be prepared according the procedures disclosed by Lütke and coworker (*Macromol. Biosci.* 2005, 5, 384-393).

Scheme IV illustrates a procedure to prepare a poly(2-oxazoline-co-ethyleneimine)-epichlorohydrin copolymer of the invention.

Scheme IV

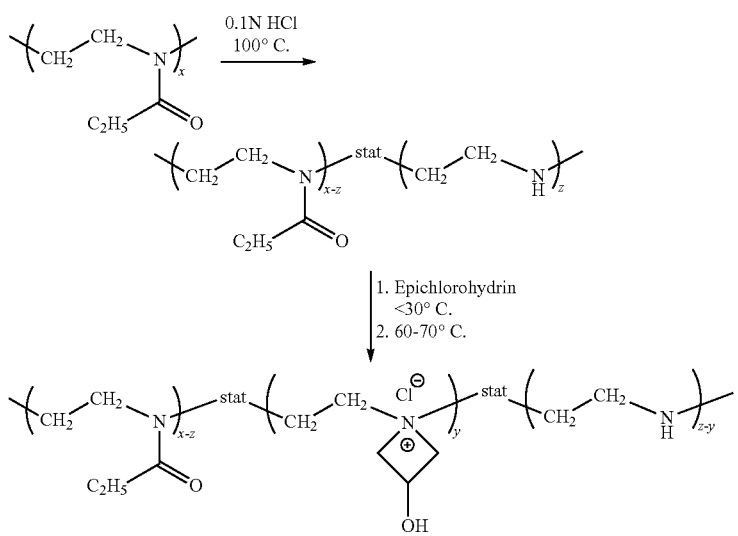

It should be understood that the two terminal groups of a poly(2-oxazoline-co-ethyleneimine)-epichlorohydrin copolymer can be present in the copolymer due to the use of cationic-ring-opening-polymerization initiator and terminator in its preparation and are not shown in Scheme IV.

In a preferred embodiment, a poly(2-oxazoline-co-ethyleneimine)-epichlorohydrin copolymer of the invention comprises hydrophilic N-acyl-iminoethylene monomeric units of formula

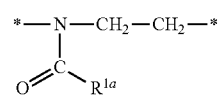

in which $R^{1a}$ is hydrogen, methyl, ethyl, propyl, isopropyl, N-pyrrolidonyl-$C_1$-$C_4$ alkyl, or a monovalent radical of -alk-$(OC_2H_4)_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)).

In another preferred embodiment, a poly(2-oxazoline-co-ethyleneimine)-epichlorohydrin copolymer of the invention comprises hydrophobic N-acyl-iminoethylene monomeric units of formula

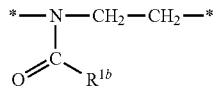

in which $R^{1b}$ is $C_6$-$C_{18}$ alkyl, $C_1$-$C_4$ alkyl-substituted phenyl, $C_1$-$C_4$-alkoxy-substituted phenyl, or $C_6$-$C_{18}$ aryl radical.

In another preferred embodiment, a poly(2-oxazoline-co-ethyleneimine)-epichlorohydrin copolymer of the invention comprises: hydrophobic N-acyl-iminoethylene monomeric units of formula

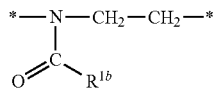

in which $R^{1b}$ is $C_6$-$C_{18}$ alkyl, $C_1$-$C_4$ alkyl-substituted phenyl, $C_1$-$C_4$-alkoxy-substituted phenyl, or $C_6$-$C_{18}$ aryl radical; and hydrophilic N-acyl-iminoethylene monomeric units of formula

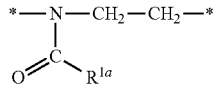

in which $R^{1a}$ is hydrogen, methyl, ethyl, propyl, isopropyl, N-pyrrolidonyl-$C_1$-$C_4$ alkyl, or a monovalent radical of -alk-$(OC_2H_4)_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)).

In various preferred embodiments of the invention, a poly(2-oxazoline-co-ethyleneimine)-epichlorohydrin copolymer of the invention comprises: (1) from about 10% to about 85%, preferably from about 20% to about 75%, even more preferably from about 30% to about 65%, by mole of N-acyl-iminoethylene monomeric units; (2) from about 2.5% to about 75%, preferably from about 5% to about 75%, even more preferably from about 10% to about 60%, by mole of azetidinium monomeric units; (3) from 0% to about 60%, preferably from 0% to about 30%, even more preferably from 0 to about 10%, by mole of ethyleneimine monomeric units; and (4) from 0 to about 5%, preferably from 0 to about 2.5%, even more preferably from 0 to about 1%, by mole of crosslink units. It is understood that these various preferred embodiments of the invention encompass various combinations of one preferred or even more preferred embodiment of one composition component (e.g., component (1), (2), (3) or (4)) can be combined with the preferred or even more preferred embodiments of other composition components).

The weight average molecular weight $M_w$ of a poly(2-oxazoline-co-ethyleneimine)-epichlorohydrin copolymer of the invention is at least about 500 Daltons, preferably from about 1,000 to about 5,000,000 Daltons, more preferably from about 5,000 to about 2,000,000 Daltons, even more preferably from about 10,000 to about 1,000,000 Daltons.

A poly(2-oxazoline-co-ethyleneimine)-epichlorohydrin copolymer of the invention can find particular use in forming non-silicone hydrogel coatings on silicone hydrogel contact lenses and/or in forming an anchoring prime coating on silicone hydrogel contact lenses.

Where a poly(2-oxazoline-co-ethyleneimine)-epichlorohydrin copolymer of the invention comprises hydrophobic N-acyl-iminoethylene monomeric units of formula

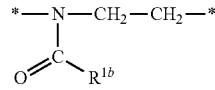

in which $R^{1b}$ is $C_6$-$C_{18}$ alkyl, $C_1$-$C_4$ alkyl-substituted phenyl, $C_1$-$C_4$-alkoxy-substituted phenyl, or $C_6$-$C_{18}$ aryl radical, such a copolymer can be used as an anchoring prime coating on silicone hydrogel contact lenses through hydrophobic-hydrophobic interactions with the hydrophobic silicone hydrogel materials at and near the surface of the silicone hydrogel contact lenses.

Where a poly(2-oxazoline-co-ethyleneimine)epichlorohydrin copolymer of the invention comprises hydrophilic N-acyl-iminoethylene monomeric units of formula

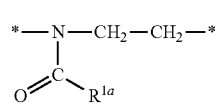

in which $R^{1a}$ is methyl, ethyl, propyl, N-pyrrolidonyl-$C_1$-$C_4$ alkyl, a monovalent radical of -alk-$(OC_2H_4)_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)), such a copolymer can be used as a coating material for forming a hydrogel coating on top of an anchoring coating (layer) on a silicone hydrogel contact lens.

Where a poly(2-oxazoline-co-ethyleneimine)-epichlorohydrin copolymer of the invention comprises both (a) hydrophobic N-acyl-iminoethylene monomeric units of formula

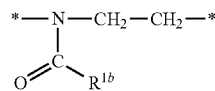

in which $R^{1b}$ is $C_6$-$C_{18}$ alkyl, $C_1$-$C_4$ alkyl-substituted phenyl, $C_1$-$C_4$-alkoxy-substituted phenyl, or $C_6$-$C_{18}$ aryl radical and (b) hydrophilic N-acyl-iminoethylene monomeric units of formula

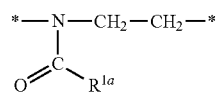

in which $R^{1a}$ is methyl, ethyl, propyl, N-pyrrolidonyl-$C_1$-$C_4$ alkyl, a monovalent radical of -alk-$(OC_2H_4)_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)), such a copolymer is an amphiphilic copolymer which can be used as a coating material for forming a hydrogel coating directly on a silicone hydrogel contact lens.

A poly(2-oxazoline-co-ethyleneimine)-epichlorohydrin copolymer of the invention can find particular use in forming a water-soluble and thermally crosslinkable hydrophilic polymeric material containing azetidinium groups. Such a water-soluble and thermally crosslinkable hydrophilic polymeric material can be obtained by chemically modifying poly(2-oxazoline-co-ethyleneimine)-epichlorohydrin copolymer of the invention with a hydrophilicity-enhancing agent having at least one reactive functional group selected from the group consisting of amino group, carboxyl group, thiol group, and combination thereof and can be especially useful for forming relatively-thick and soft non-silicone hydrogel coatings on contact lenses, preferably hydrogel contact lenses, more preferably silicone hydrogel contact lenses.

The invention, in another aspect, provides a water-soluble and thermally-crosslinkable hydrophilic polymeric material which comprises: azetidinium groups; from about 5% to about 95%, preferably from about 10% to about 90%, more preferably from about 15% to about 85%, by weight of first polymer chains derived from a poly(2-oxazoline-co-ethyleneimine)-epichlorohydrin copolymer of any one of claims 1 to 6; and from about 5% to about 95%, preferably from about 10% to about 90%, even more preferably from about 15% to about 85%, by weight of hydrophilic moieties or second polymer chains derived from at least one hydrophilicity-enhancing agent having at least one reactive functional group selected from the group consisting of primary amino group, secondary amino group, carboxyl group, thiol group, and combination thereof. The composition of the hydrophilic polymeric material is determined by the composition (based on the total weight of the reactants) of a reactants mixture used for preparing the thermally-crosslinkable hydrophilic polymeric material according to the crosslinking reactions shown in Scheme I above. For example, if a reactant mixture comprises about 75% by weight of a poly(2-oxazoline-co-ethyleneimine)-epichlorohydrin copolymer of the invention and about 25% by weight of at least one hydrophilicity-enhancing agent based on the total weight of the reactants, then the resultant hydrophilic polymeric material comprise about 75% by weight of first polymer chains derived from the poly(2-oxazoline-co-ethyleneimine)-epichlorohydrin copolymer of the invention and about 25% by weight of hydrophilic moieties or second polymer chains derived from said at least one hydrophilicity-enhancing agent. The azetidinium groups of the thermally-crosslinkable hydrophilic polymeric material are those azetidinium groups (of the epichlorohydrin-functionalized polyamine or polyamidoamine) which do not participate in crosslinking reactions for preparing the thermally-crosslinkable hydrophilic polymeric material.

Any suitable hydrophilicity-enhancing agents can be used in the invention so long as they contain at least one amino group, at least one carboxyl group, and/or at least one thiol group.

A preferred class of hydrophilicity-enhancing agents include without limitation: primary amino-, secondary amino-, carboxyl- or thiol-containing monosaccharides (e.g., 3-amino-1,2-propanediol, 1-thiolglycerol, 5-keto-D-gluconic acid, galactosamine, glucosamine, galacturonic acid, gluconic acid, glucosaminic acid, mannosamine, saccharic acid 1,4-lactone, saccharide acid, Ketodeoxynonulosonic acid, N-methyl-D-glucamine, 1-amino-1-deoxy-3-D-galactose, 1-amino-1-deoxysorbitol, 1-methylamino-1-deoxysorbitol, N-aminoethyl gluconamide); primary amino-, secondary amino-, carboxyl- or thiol-containing disaccharides (e.g., chondroitin disaccharide sodium salt, di(β-D-xylopyranosyl)amine, digalacturonic acid, heparin disaccharide, hyaluronic acid disaccharide, Lactobionic acid); and primary amino-, secondary amino-, carboxyl- or thiol-containing oligosaccharides (e.g., carboxymethyl-β-cyclodextrin sodium salt, trigalacturonic acid); and combinations thereof.

Another preferred class of hydrophilicity-enhancing agents is hydrophilic polymers having one or more (primary or secondary) amino, carboxyl and/or thiol groups. More preferably, the content of the amino (—NHR' with R' as defined above), carboxyl (—COOH) and/or thiol (—SH) groups in a hydrophilic polymer as a hydrophilicity-enhancing agent is less than about 40%, preferably less than about 30%, more preferably less than about 20%, even more preferably less than about 10%, by weight based on the total weight of the hydrophilic polymer.

One preferred class of hydrophilic polymers as hydrophilicity-enhancing agents are (primary or secondary) amino- or carboxyl-containing polysaccharides, for example, such as, carboxymethylcellulose (having a carboxyl content of about 40% or less, which is estimated based on the composition of repeating units, —[$C_6H_{10-m}O_5(CH_2CO_2H)_m$]— in which m is 1 to 3), carboxyethylcellulose (having a carboxyl content of about 36% or less, which is estimated based on the composition of repeating units, —[$C_6H_{10-m}O_5(C_2H_4CO_2H)_m$]— in which m is 1 to 3) carboxypropylcellulose (having a carboxyl content of about 32% or less, which is estimated based on the composition of repeating units, —[$C_6H_{10-m}O_5(C_3H_6CO_2H)_m$]—, in which m is 1 to 3), hyaluronic acid (having a carboxyl content of about 11%, which is estimated based on the composition of repeating units, —($C_{13}H_{20}O_9NCO_2H$)—), chondroitin sulfate (having a carboxyl content of about 9.8%, which is estimated based on the composition of repeating units, —($C_{12}H_{18}O_{13}NSCO_2H$)—), or combinations thereof.

Another preferred class of hydrophilic polymers as hydrophilicity-enhancing agents include without limitation: poly(ethylene glycol) (PEG) with mono-amino (primary or secondary amino), carboxyl or thiol group (e.g., PEG-NH$_2$, PEG-SH, PEG-COOH); H$_2$N-PEG-NH$_2$; HOOC-PEG-COOH; HS-PEG-SH; H$_2$N-PEG-COOH; HOOC-PEG-SH; H$_2$N-PEG-SH; multi-arm PEG with one or more amino (primary or secondary), carboxyl or thiol groups; PEG dendrimers with one or more amino (primary or secondary), carboxyl or thiol groups; a diamino-(primary or secondary) or dicarboxyl-terminated homo- or co-polymer of a non-reactive hydrophilic vinylic monomer; a monoamino-(primary or secondary) or monocarboxyl-terminated homo- or co-polymer of a non-reactive hydrophilic vinylic monomer; a copolymer which is a polymerization product of a composition comprising (1) about 60% by weight or less, preferably from about 0.1% to about 30%, more preferably from about 0.5% to about 20%, even more preferably from about 1% to about 15%, by weight of one or more reactive vinylic monomers and (2) at least one non-reactive hydrophilic vinylic monomer; and combinations thereof. Reactive vinylic monomer(s) and non-reactive hydrophilic vinylic monomer(s) are those described previously.

More preferably, a hydrophilic polymer as a hydrophilicity-enhancing agent is PEG-NH$_2$; PEG-SH; PEG-COOH; H$_2$N-PEG-NH$_2$; HOOC-PEG-COOH; HS-PEG-SH; H$_2$N-PEG-COOH; HOOC-PEG-SH; H$_2$N-PEG-SH; multi-arm PEG with one or more amino, carboxyl or thiol groups; PEG dendrimers with one or more amino, carboxyl or thiol groups; a monoamino-, monocarboxyl-, diamino- or dicarboxyl-terminated homo- or copolymer of a non-reactive hydrophilic vinylic monomer selected from the group consisting of acryamide (AAm), N,N-dimethylacrylamide (DMA), N-vinylpyrrolidone (NVP), N-vinyl-N-methyl acetamide, glycerol (meth)acrylate, hydroxyethyl (meth)acrylate, N-hydroxyethyl (meth)acrylamide, $C_1$-$C_4$-alkoxy polyethylene glycol (meth)acrylate having a weight average molecular weight of up to 400 Daltons, vinyl alcohol, N-methyl-3-methylene-2-pyrrolidone, 1-methyl-5-methylene-2-pyrrolidone, 5-methyl-3-methylene-2-pyrrolidone, N,N-dimethylaminoethyl (meth)acrylate, N,N-dimethylaminopropyl (metha)crylamide, (meth)acryloyloxyethyl phosphorylcholine, and combinations thereof; a copolymer which is a polymerization product of a composition comprising (1) from about 0.1% to about 30%, preferably from about 0.5% to about 20%, more preferably from about 1% to about 15%, by weight of acrylic acid, $C_1$-$C_3$ alkylacrylic acid, allylamine and/or amino-$C_2$-$C_4$ alkyl (meth)acrylate, and (2) at least one non-reactive hydrophilic vinylic monomer selected from the group consisting of acryamide, N,N-dimethylacrylamide, N-vinylpyrrolidone, (meth)acryloyloxyethyl phosphorylcholine, N-vinyl-N-methyl acetamide, glycerol (meth)acrylate, hydroxyethyl (meth)acrylate, N-hydroxyethyl (meth)acrylamide, $C_1$-$C_4$-alkoxy polyethylene glycol (meth)acrylate having a weight average molecular weight of up to 400 Daltons, vinyl alcohol, and combination thereof.

Most preferably, the hydrophilicity-enhancing agent as a hydrophilicity-enhancing agent is PEG-$NH_2$; PEG-SH; PEG-COOH; monoamino-, monocarboxyl-, diamino- or dicarboxyl-terminated polyvinylpyrrolidone; monoamino-, monocarboxyl-, diamino- or dicarboxyl-terminated polyacrylamide; monoamino-, monocarboxyl-, diamino- or dicarboxyl-terminated poly(DMA); monoamino- or monocarboxyl-, diamino- or dicarboxyl-terminated poly(DMA-co-NVP); monoamino-, monocarboxyl-, diamino- or dicarboxyl-terminated poly(NVP-co-N,N-dimethylaminoethyl (meth)acrylate)); monoamino-, monocarboxyl-, diamino- or dicarboxyl-terminated poly(vinylalcohol); monoamino-, monocarboxyl-, diamino- or dicarboxyl-terminated poly[(meth)acryloyloxyethyl phosphrylcholine] homopolymer or copolymer; monoamino-, monocarboxyl-, diamino- or dicarboxyl-terminated poly(NVP-co-vinyl alcohol); monoamino-, monocarboxyl-, diamino- or dicarboxyl-terminated poly(DMA-co-vinyl alcohol); poly[(meth)acrylic acid-co-acrylamide] with from about 0.1% to about 30%, preferably from about 0.5% to about 20%, more preferably from about 1% to about 15%, by weight of (meth)acrylic acid; poly[(meth)acrylic acid-co-NVP] with from about 0.1% to about 30%, preferably from about 0.5% to about 20%, more preferably from about 1% to about 15%, by weight of (meth)acrylic acid; a copolymer which is a polymerization product of a composition comprising (1) (meth)acryloyloxyethyl phosphorylcholine and (2) from about 0.1% to about 30%, preferably from about 0.5% to about 20%, more preferably from about 1% to about 15%, by weight of acrylic acid, $C_1$-$C_3$ alkylacrylic acid, allylamine and/or amino-$C_2$-$C_4$alkyl (meth)acrylate; and combination thereof.

PEGs with functional groups and multi-arm PEGs with functional groups can be obtained from various commercial suppliers, e.g., Polyscience, and Shearwater Polymers, inc., etc.

Monoamino-, monocarboxyl-, diamino- or dicarboxyl-terminated homo- or copolymers of one or more non-reactive hydrophilic vinylic monomers or of a phosphorylcholine-containing vinylic monomer can be prepared according to procedures described in U.S. Pat. No. 6,218,508, herein incorporated by reference in its entirety. For example, to prepare a diamino- or dicarboxyl-terminated homo- or co-polymer of a non-reactive hydrophilic vinylic monomer, the non-reactive vinylic monomer, a chain transfer agent with an amino or carboxyl group (e.g., 2-aminoethanethiol, 2-mercaptopropinic acid, thioglycolic acid, thiolactic acid, or other hydroxymercaptanes, aminomercaptans, or carboxyl-containing mercaptanes) and optionally other vinylic monomer are copolymerized (thermally or actinically) with a reactive vinylic monomer (having an amino or carboxyl group), in the presence of an free-radical initiator. Generally, the molar ratio of chain transfer agent to that of all of vinylic monomers other than the reactive vinylic monomer is from about 1:5 to about 1:100, whereas the molar ratio of chain transfer agent to the reactive vinylic monomer is 1:1. In such preparation, the chain transfer agent with amino or carboxyl group is used to control the molecular weight of the resultant hydrophilic polymer and forms a terminal end of the resultant hydrophilic polymer so as to provide the resultant hydrophilic polymer with one terminal amino or carboxyl group, while the reactive vinylic monomer provides the other terminal carboxyl or amino group to the resultant hydrophilic polymer. Similarly, to prepare a monoamino- or monocarboxyl-terminated homo- or co-polymer of a non-reactive hydrophilic vinylic monomer, the non-reactive vinylic monomer, a chain transfer agent with an amino or carboxyl group (e.g., 2-aminoethanethiol, 2-mercaptopropinic acid, thioglycolic acid, thiolactic acid, or other hydroxymercaptanes, aminomercaptans, or carboxyl-containing mercaptanes) and optionally other vinylic monomers are copolymerized (thermally or actinically) in the absence of any reactive vinylic monomer.

As used herein, a copolymer of a non-reactive hydrophilic vinylic monomer refers to a polymerization product of a non-reactive hydrophilic vinylic monomer with one or more additional vinylic monomers. Copolymers comprising a non-reactive hydrophilic vinylic monomer and a reactive vinylic monomer (e.g., a carboxyl-containing vinylic monomer, a primary amino group-containing vinylic monomer or a secondary amino group-containing vinylic monomer) can be prepared according to any well-known radical polymerization methods or obtained from commercial suppliers. Copolymers containing methacryloyloxyethyl phosphorylcholine and carboxyl-containing vinylic monomer (or amino-containing vinylic monomer) can be obtained from NOP Corporation (e.g., LIPIDURE®-A and -AF).

The weight average molecular weight $M_w$ of the hydrophilic polymer having at least one amino, carboxyl or thiol group (as a hydrophilicity-enhancing agent) is preferably from about 500 to about 1,000,000, more preferably from about 1,000 to about 500,000, even more preferably from about 5,000 to about 250,000 Daltons.

In accordance with the invention, the reaction between a hydrophilicity-enhancing agent and a poly(2-oxazoline-co-ethyleneimine)-epichlorohydrin copolymer of the invention is carried out at a temperature of from about 40° C. to about 100° C. for a period of time sufficient (from about 0.3 hour to about 24 hours, preferably from about 1 hour to about 12 hours, even more preferably from about 2 hours to about 8 hours) to form a water-soluble and thermally-crosslinkable hydrophilic polymeric material containing azetidinium groups.

In accordance with the invention, the concentration of a hydrophilicity-enhancing agent relative to a poly(2-oxazoline-co-ethyleneimine)-epichlorohydrin copolymer of the invention must be selected not to render a resultant hydrophilic polymeric material water-insoluble (i.e., a solubility of less than 0.005 g per 100 ml of water at room temperature) and not to consume more than about 99%, preferably about 98%, more preferably about 97%, even more preferably about 96% of the azetidinium groups of the poly(2-oxazoline-co-ethyleneimine)-epichlorohydrin copolymer of the invention.

The invention, in a further aspect, provides methods for producing coated contact lenses (preferably hydrogel contact lenses, more preferably silicone hydrogel contact lenses) each having a crosslinked hydrophilic coating thereon, involving use of at least a poly(2-oxazoline-co-ethyleneimine)-epichlorohydrin copolymer of the invention fully described above and/or at least one water-soluble and thermally crosslinkable hydrophilic polymeric material of the invention fully described above.

One method of the invention for producing coated contact lenses (preferably hydrogel contact lenses, more preferably silicone hydrogel contact lenses) each having a crosslinked hydrophilic coating thereon comprises the steps of: (a) obtaining a contact lens (preferably a hydrogel contact lens, more preferably a silicone hydrogel contact lens) and a poly(2-oxazoline-co-ethyleneimine)-epichlorohydrin copolymer of the invention as described above (incorporated herein in its entirety), wherein the contact lens comprises, on and/or near the surface of the contact lens, reactive functional groups selected from the group consisting of primary amino groups, secondary amino groups, carboxyl groups, and combinations thereof; and (b) heating the contact lens in an aqueous solution in the presence of the poly(2-oxazoline-co-ethyleneimine)-epichlorohydrin copolymer to and at a temperature from about 40° C. to about 140° C. for a period of time sufficient to covalently attach the poly(2-oxazoline-co-ethyleneimine)-epichlorohydrin copolymer onto the surface of the contact lens through covalent linkages each formed between one azetidinium group of the poly(2-oxazoline-co-ethyleneimine)-epichlorohydrin copolymer and one of the reactive functional groups on and/or near the surface of the contact lens, thereby forming a crosslinked hydrophilic coating on the contact lens.

Another method of the invention for producing coated contact lenses (preferably hydrogel contact lenses, more preferably silicone hydrogel contact lenses) each having a crosslinked hydrophilic coating thereon comprises the steps of: (a) obtaining a contact lens (preferably a hydrogel contact lens, more preferably a silicone hydrogel contact lens); (b) applying a layer of a poly(2-oxazoline-co-ethyleneimine)-epichlorohydrin copolymer of the invention to form an anchoring coating on the contact lens, wherein the poly(2-oxazoline-co-ethyleneimine)-epichlorohydrin copolymer comprises hydrophobic N-acyl-iminoethylene monomeric units as described above ((incorporated herein in its entirety); and (c) heating the contact lens having the anchoring coating thereon in an aqueous solution to and at a temperature from about 40° C. to about 140° C. in the presence of a water-soluble hydrophilic polymer having reactive functional groups selected from the group consisting of primary amino groups, secondary amino groups, carboxyl groups, thiol groups, and combinations thereof, for a period of time sufficient to covalently attach the hydrophilic polymer onto the surface of the contact lens through covalent linkages each formed between one azetidinium group of the anchoring coating and one of the reactive functional groups of the hydrophilic polymer, thereby forming a crosslinked hydrophilic coating on the contact lens.

A further method of the invention for producing coated contact lenses (preferably hydrogel contact lenses, more preferably silicone hydrogel contact lenses) each having a crosslinked hydrophilic coating thereon comprises the steps of: (a) obtaining a contact lens (preferably a hydrogel contact lens, more preferably a silicone hydrogel contact lens) and a water-soluble and thermally-crosslinkable hydrophilic polymeric material of the invention as described above (incorporated herein in its entirety), wherein the contact lens comprises, on and/or near the surface of the contact lens, reactive functional groups selected from the group consisting of primary amino groups, secondary amino groups, carboxyl groups, and combinations thereof; and (b) heating the contact lens in an aqueous solution in the presence of the water-soluble and thermally-crosslinkable hydrophilic polymeric material to and at a temperature from about 40° C. to about 140° C. for a period of time sufficient to covalently attach the hydrophilic polymeric material onto the surface of the contact lens through covalent linkages each formed between one azetidinium group of the poly(2-oxazoline-co-ethyleneimine)-epichlorohydrin copolymer and one of the reactive functional groups on and/or near the surface of the contact lens, thereby forming a crosslinked hydrophilic coating on the contact lens.

A person skilled in the art knows very well how to make contact lenses. For example, contact lenses can be produced in a conventional "spin-casting mold," as described for example in U.S. Pat. No. 3,408,429, or by the full cast-molding process in a static form, as described in U.S. Pat. Nos. 4,347,198; 5,508,317; 5,583,463; 5,789,464; and 5,849,810, or by lathe cutting of silicone hydrogel buttons as used in making customized contact lenses. In cast-molding, a lens formulation typically is dispensed into molds and cured (i.e., polymerized and/or crosslinked) in molds for making contact lenses. For producing hydrogel contact lenses, a hydrogel lens formulation comprises at least one hydrophilic vinylic monomer. For production of silicone hydrogel (SiHy) contact lenses, a SiHy lens-forming composition (or SiHy lens formulation) for cast-molding or spin-cast molding or for making SiHy rods used in lathe-cutting of contact lenses generally comprises at least one components selected from the group consisting of a silicone-containing vinylic monomer, a silicone-containing vinylic macromer, a silicone-containing prepolymer, a hydrophilic vinylic monomer, a hydrophobic vinylic monomer, a cross-linking agent (a compound having a molecular weight of about 700 Daltons or less and containing at least two ethylenically unsaturated groups), a free-radical initiator (photoinitiator or thermal initiator), a hydrophilic vinylic macromer/prepolymer, and combination thereof, as well known to a person skilled in the art. A SiHy contact lens formulation can also comprise other necessary components known to a person skilled in the art, such as, for example, a UV-absorbing agent, a visibility tinting agent (e.g., dyes, pigments, or mixtures thereof), antimicrobial agents (e.g., preferably silver nanoparticles), a bioactive agent, leachable lubricants, leachable tear-stabilizing agents, and mixtures thereof, as known to a person skilled in the art. Resultant SiHy contact lenses then can be subjected to extraction with an extraction solvent to remove unpolymerized components from the resultant lenses and to hydration process, as known by a person skilled in the art. In addition, a preformed SiHy contact lens can be a colored contact lens (i.e., a SiHy contact lens having at least one colored patterns printed thereon as well known to a person skilled in the art).

Numerous SiHy lens formulations including various combinations of components described above have been described in numerous patents and patent applications published by the filing date of this application. All of them can be used in obtaining a SiHy lens to be coated. A SiHy lens formulation for making commercial SiHy lenses, such as, lotrafilcon A, lotrafilcon B, delefilcon A, balafilcon A, galyfilcon A, senofilcon A, narafilcon A, narafilcon B, comfilcon A, enfilcon A, asmofilcon A, or the like, can also be used in making SiHy contact lenses to be coated in this invention.

In accordance with the invention, a contact lens (preferably a hydrogel contact lens, more preferably a silicone hydrogel contact lens) can inherently comprise reactive functional groups (primary amino groups, secondary amino groups, and/or carboxyl groups) on and/or near its surface, or can be free of but be modified to comprise reactive functional groups (primary amino groups, secondary amino groups, and/or carboxyl groups) on and/or near its surface.

Where a contact lens (preferably a hydrogel contact lens, more preferably a silicone hydrogel contact lens) inherently comprises reactive functional groups (primary amino groups, secondary amino groups, and/or carboxyl groups) on and/or near its surface, it is obtained by polymerizing a lens formulation comprising a reactive vinylic monomer (i.e., a vinylic monomer having a reactive functional group selected from the group consisting of primary amino group, secondary amino group, and carboxyl group).

Examples of preferred reactive vinylic monomers include without limitation amino-$C_2$-$C_6$ alkyl (meth)acrylate, $C_1$-$C_6$ alkylamino-$C_2$-$C_6$ alkyl (meth)acrylate, allylamine, vinylamine, amino-$C_2$-$C_6$ alkyl (meth)acrylamide, $C_1$-$C_6$ alkylamino-$C_2$-$C_6$ alkyl (meth)acrylamide, acrylic acid, $C_1$-$C_4$ alkylacrylic acid (e.g., methacrylic ethylacrylic acid, propylacrylic acid, butylacrylic acid), N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carboxy-4-phenyl butadiene-1,3, itaconic acid, citraconic acid, mesaconic acid, glutaconic acid, aconitic acid, maleic acid, fumaric acid, tricarboxy ethylene, and combinations thereof. Preferably, the silicone hydrogel contact lens is made from a lens formulation comprising at least one reactive vinylic monomer selected from the group consisting of amino-$C_2$-$C_6$ alkyl (meth)acrylate, $C_1$-$C_6$ alkylamino-$C_2$-$C_6$ alkyl (meth)acrylate, allylamine, vinylamine, amino-$C_1$-$C_6$ alkyl (meth)acrylamide, $C_1$-$C_6$ alkylamino-$C_2$-$C_6$ alkyl (meth)acrylamide, acrylic acid, $C_1$-$C_6$ alkylacrylic acid, N,N-2-acrylamidoglycolic acid, and combinations thereof. The lens formulation comprises preferably from about 0.1% to about 10%, more preferably from about 0.25% to about 7%, even more preferably from about 0.5% to about 5%, most preferably from about 0.75% to about 3%, by weight of the reactive vinylic monomer.

A contact lens can also be subjected either to a surface treatment to form a reactive base coating having amino groups and/or carboxyl groups on the surface of the contact lens. Examples of surface treatments include without limitation a surface treatment by energy (e.g., a plasma, a static electrical charge, irradiation, or other energy source), chemical treatments, chemical vapor deposition, the grafting of hydrophilic vinylic monomers or macromers onto the surface of an article, layer-by-layer coating ("LbL coating") obtained according to methods described in U.S. Pat. Nos. 6,451,871, 6,719,929, 6,793,973, 6,811,805, and 6,896,926 and in U.S. Patent Application Publication Nos. 2007/0229758A1, 2008/0152800A1, and 2008/0226922A1, (herein incorporated by references in their entireties). "LbL coating", as used herein, refers to a coating that is not covalently attached to the polymer matrix of a contact lens and is obtained through a layer-by-layer ("LbL") deposition of charged or chargeable (by protonation or deprotonation) and/or non-charged materials on the lens. An LbL coating can be composed of one or more layers.

Preferably, the surface treatment is an LbL coating process. In this preferred embodiment (i.e., the reactive LbL base coating embodiment), a resultant contact lens comprises a reactive LbL base coating including at least one layer of a reactive polymer (i.e., a polymer having pendant reactive functional groups such as primary amino groups, secondary amino groups, and/or carboxyl groups), wherein the reactive LbL base coating is obtained by contacting the contact lens with a coating solution of a reactive polymer. Contacting of a contact lens with a coating solution of a reactive polymer can occur by dipping it into the coating solution or by spraying it with the coating solution. One contacting process involves solely dipping the contact lens in a bath of a coating solution for a period of time or alternatively dipping the contact lens sequentially in a series of bath of coating solutions for a fixed shorter time period for each bath. Another contacting process involves solely spray a coating solution. However, a number of alternatives involve various combinations of spraying- and dipping-steps may be designed by a person having ordinary skill in the art. The contacting time of a contact lens with a coating solution of a reactive polymer may last up to about 10 minutes, preferably from about 5 to about 360 seconds, more preferably from about 5 to about 250 seconds, even more preferably from about 5 to about 200 seconds.

In accordance with this reactive LbL base coating embodiment, the reactive polymer can be a linear or branched polymer having pendant reactive functional groups (primary amino groups, secondary amino groups, and/or carboxyl groups). Any polymers having pendant reactive functional groups (primary amino groups, secondary amino groups, and/or carboxyl groups) can be used as a reactive polymer for forming base coatings on silicone hydrogel contact lenses. Examples of such reactive polymers include without limitation: a homopolymer of a reactive vinylic monomer; a copolymer of two or more reactive vinylic monomers; a copolymer of a reactive vinylic monomer with one or more non-reactive hydrophilic vinylic monomers (i.e., hydrophilic vinylic monomers free of any carboxyl or (primary or secondary) amino group); polyethyleneimine (PEI); polyvinylalcohol with pendant amino groups; a carboxyl-containing cellulose (e.g., carboxymethylcellulose, carboxyethylcellulose, carboxypropylcellulose); hyaluronate; chondroitin sulfate; poly(glutamic acid); poly (aspartic acid); and combinations thereof.

Preferred reactive vinylic monomers are those described previously.

Preferred examples of non-reactive hydrophilic vinylic monomers free of carboxyl or amino group include without limitation acrylamide (AAm), methacrylamide N,N-dimethylacrylamide (DMA), N,N-dimethylmethacrylamide (DMMA), N-vinylpyrrolidone (NVP), N,N-dimethylaminoethylmethacrylate (DMAEM), N,N-dimethylaminoethylacrylate (DMAEA), N,N-dimethylaminopropylmethacrylamide (DMAPMAm), N,N-dimethylaminopropylacrylamide (DMAPAAm), glycerol methacrylate, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, hydroxypropyl (meth)acrylate, $C_1$-$C_4$-alkoxy polyethylene glycol (meth)acrylate having a weight average molecular weight of up to 1500 Daltons, N-vinyl formamide, N-vinyl acetamide, N-vinyl isopropylamide, N-vinyl-N-methyl acetamide, allyl alcohol, vinyl alcohol (hydrolyzed form of vinyl acetate in the copolymer), a phosphorylcholine-containing vinylic monomer (including (meth)acryloyloxyethyl phosphorylcholine and those described in U.S. Pat. No. 5,461,433, herein incorporated by reference in its entirety), and combinations thereof.

Preferably, the reactive polymers for forming a reactive LbL base coating are polyacrylic acid, polymethacrylic acid, polyethylacrylic acid, polypropylacrylic acid, poly(N,N-2-acrylamidoglycolic acid), poly[(meth)acrylic acid-co-acrylamide], poly[(meth)acrylic acid-co-vinylpyrrolidone], hydrolyzed poly[(meth)acrylic acid-co-vinylacetate], polyethyleneimine (PEI), polyallylamine hydrochloride (PAH) homo- or copolymer, polyvinylamine homo- or copolymer, or combinations thereof.

The weight average molecular weight $M_w$ of a reactive polymer for forming a reactive LbL base coating is at least about 10,000 Daltons, preferably at least about 50,000 Daltons, more preferably at least about 100,000 Daltons, even more preferably from about 500,000 to 5,000,000 Daltons.

A solution of a reactive polymer for forming a reactive LbL base coating on contact lenses can be prepared by dissolving one or more reactive polymers in water, a mixture of water and an organic solvent miscible with water, an organic solvent, or a mixture of one or more organic solvent. Preferably, the reactive polymer is dissolved in a mixture of water and one or more organic solvents, an organic solvent, or a mixture of one or more organic solvent. It is believed that a solvent system containing at least one organic solvent can swell a contact lens (preferably hydrogel contact lens, more preferably a silicone hydrogel contact lens) so that a portion of the reactive polymer may penetrate into the contact lens and increase the durability of the reactive base coating.

Any organic solvents can be used in preparation of a solution of the reactive polymer. Examples of organic solvents include without limitation tetrahydrofuran, tripropylene glycol methyl ether, dipropylene glycol methyl ether, ethylene glycol n-butyl ether, ketones (e.g., acetone, methyl ethyl ketone, etc.), diethylene glycol n-butyl ether, diethylene glycol methyl ether, ethylene glycol phenyl ether, propylene glycol methyl ether, propylene glycol methyl ether acetate, dipropylene glycol methyl ether acetate, propylene glycol n-propyl ether, dipropylene glycol n-propyl ether, tripropylene glycol n-butyl ether, propylene glycol n-butyl ether, dipropylene glycol n-butyl ether, tripropylene glycol n-butyl ether, propylene glycol phenyl ether dipropylene glycol dimethyl ether, polyethylene glycols, polypropylene glycols, ethyl acetate, butyl acetate, amyl acetate, methyl lactate, ethyl lactate, i-propyl lactate, methylene chloride, methanol, ethanol, 1- or 2-propanol, 1- or 2-butanol, tert-butanol, tert-amyl alcohol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, 1-ethoxy-2-propanol, 1-methyl-2-pyrrolidone, N,N-dimethylpropionamide, dimethyl formamide, dimethyl acetamide, dimethyl propionamide, N-methyl pyrrolidinone, and mixtures thereof.

In another preferred embodiment, a contact lens (preferably a hydrogel contact lens, more preferably a silicone hydrogel contact lens) comprises inherently reactive functional groups (primary amino groups, secondary amino groups, and/or carboxyl groups) on and/or near its surface and is further subjected to a surface treatment to form a reactive LbL base coating having reactive functional groups therein.

In another preferred embodiment (reactive plasma base coating), a contact lens (preferably a hydrogel contact lens, more preferably a silicone hydrogel contact lens) is subjected to a plasma treatment to form a covalently-attached reactive plasma base coating on the contact lens, i.e., polymerizing one or more reactive vinylic monomers (any one of those described previously) under the effect of plasma generated by electric discharge (so-called plasma-induced polymerization). The term "plasma" denotes an ionized gas, e.g. created by electric glow discharge which may be composed of electrons, ions of either polarity, gas atoms and molecules in the ground or any higher state of any form of excitation, as well as of photons. It is often called "low temperature plasma". For a review of plasma polymerization and its uses reference is made to R. Hartmann "Plasma polymerisation: Grundlagen, Technik und Anwendung, Jahrb. Oberflächentechnik (1993) 49, pp. 283-296, Battelle-Inst. e.V. Frankfurt/Main Germany; H. Yasuda, "Glow Discharge Polymerization", Journal of Polymer Science: Macromolecular Reviews, vol. 16 (1981), pp. 199-293; H. Yasuda, "Plasma Polymerization", Academic Press, Inc. (1985); Frank Jansen, "Plasma Deposition Processes", in "Plasma Deposited Thin Films", ed. by T. Mort and F. Jansen, CRC Press Boca Raton (19); O. Auciello et al. (ed.) "Plasma-Surface Interactions and Processing of Materials" publ. by Kluwer Academic Publishers in NATO ASI Series; Series E: Applied Sciences, vol. 176 (1990), pp. 377-399; and N. Dilsiz and G. Akovali "Plasma Polymerization of Selected Organic Compounds", Polymer, vol. 37 (1996) pp. 333-341. Preferably, the plasma-induced polymerization is an "after-glow" plasma-induced polymerization as described in WO98028026 (herein incorporated by reference in its entirety). For "after-glow" plasma polymerization the surface of a contact lens is treated first with a non-polymerizable plasma gas (e.g. H2, He or Ar) and then in a subsequent step the surface thus activated is exposed to a vinylic monomer having an amino group or carboxyl group (any reactive vinylic monomer described above), while the plasma power having been switched off. The activation results in the plasma-induced formation of radicals on the surface which in the subsequent step initiate the polymerization of the vinylic monomer thereon.

In accordance with the invention, an anchoring coating on a contact lens (preferably a hydrogel contact lens, more preferably a silicone hydrogel contact lens) is formed by contacting a contact lens (to be coated) with a solution of a poly(2-oxazoline-co-ethyleneimine)-epichlorohydrin copolymer comprising hydrophobic N-acyl-iminoethylene monomeric units as described above (incorporated herein in its entirety). Contacting of the contact lens with a coating solution of a poly(2-oxazoline-co-ethyleneimine)-epichlorohydrin copolymer comprising hydrophobic N-acyl-iminoethylene monomeric units can occur by dipping it into the coating solution or by spraying it with the coating solution. One contacting process involves solely dipping the contact lens in a bath of a solution of the anchoring polymer for a period of time or alternatively dipping the contact lens sequentially in a series of bath of solutions of the anchoring polymer for a fixed shorter time period for each bath. Another contacting process involves solely spray a solution of the anchoring polymer. However, a number of alternatives involve various combinations of spraying- and dipping-steps may be designed by a person having ordinary skill in the art. The contacting time of a contact lens with a solution of the anchoring polymer may last up to about 10 minutes, preferably from about 5 to about 360 seconds, more preferably from about 5 to about 250 seconds, even more preferably from about 5 to 200 seconds. A coating solution of a poly(2-oxazoline-co-ethyleneimine)-epichlorohydrin copolymer comprising hydrophobic N-acyl-iminoethylene monomeric units can be prepared by dissolving it in an organic solvent, a mixture of two or more organic solvents, a mixture of water with one or more organic solvent. It is believed that a solvent system containing at least one organic solvent can swell a silicone hydrogel contact lens so that a portion of the poly(2-oxazoline-co-ethyleneimine)-epichlorohydrin copolymer comprising hydrophobic N-acyl-iminoethylene monomeric units may penetrate into the contact lens and increase the durability of the anchoring coating. Any organic solvent described above can be used in preparing a coating solution of a poly(2-oxazoline-co-ethyleneimine)-epichlorohydrin copolymer comprising hydrophobic N-acyl-iminoethylene monomeric units.

In accordance with this aspect of the invention, the step of heating is performed preferably by autoclaving the contact lens (preferably hydrogel contact lens, more preferably silicone hydrogel contact lens) immersed in a packaging solution (i.e., a buffered aqueous solution) in a sealed lens package at a temperature of from about 118° C. to about 125° C. for approximately 20-90 minutes. In accordance with this embodiment of the invention, the packaging solution is a buffered aqueous solution which is ophthalmically safe after autoclave.

Lens packages (or containers) are well known to a person skilled in the art for autoclaving and storing a soft contact lens. Any lens packages can be used in the invention. Preferably, a lens package is a blister package which comprises a base and a cover, wherein the cover is detachably sealed to the base, wherein the base includes a cavity for receiving a sterile packaging solution and the contact lens.

Lenses are packaged in individual packages, sealed, and sterilized (e.g., by autoclave at about 120° C. or higher for at least 30 minutes under pressure) prior to dispensing to users. A person skilled in the art will understand well how to seal and sterilize lens packages.

In accordance with the invention, a packaging solution contains at least one buffering agent and one or more other ingredients known to a person skilled in the art. Examples of other ingredients include without limitation, tonicity agents, surfactants, antibacterial agents, preservatives, and lubricants (e.g., cellulose derivatives, polyvinyl alcohol, polyvinyl pyrrolidone).

The packaging solution contains a buffering agent in an amount sufficient to maintain a pH of the packaging solution in the desired range, for example, preferably in a physiologically acceptable range of about 6 to about 8.5. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (2-amino-2-hydroxymethyl-1,3-propanediol), Bis-Tris (Bis-(2-hydroxyethyl)-imino-tris-(hydroxymethyl)-methane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N, N'-bis(2-ethanesulfonic acid), TES (N-[Tris (hydroxymethyl)methyl]-2-aminoethanesulfonic acid), salts thereof, phosphate buffers, e.g. $Na_2HPO_4$, $NaH_2PO_4$, and $KH_2PO_4$ or mixtures thereof. A preferred bis-aminopolyol is 1,3-bis(tris[hydroxymethyl]-methylamino)propane (bis-TRIS-propane). The amount of each buffer agent in a packaging solution is preferably from 0.001% to 2%, preferably from 0.01% to 1%; most preferably from about 0.05% to about 0.30% by weight.

The packaging solution has a tonicity of from about 200 to about 450 milliosmol (mOsm), preferably from about 250 to about 350 mOsm. The tonicity of a packaging solution can be adjusted by adding organic or inorganic substances which affect the tonicity. Suitable occularly acceptable tonicity agents include, but are not limited to sodium chloride, potassium chloride, glycerol, propylene glycol, polyols, mannitols, sorbitol, xylitol and mixtures thereof.

A packaging solution of the invention has a viscosity of from about 1 centipoise to about 8 centipoises, more preferably from about 1.5 centipoises to about 5 centipoises, at 25° C.

In a preferred embodiment, the packaging solution comprises preferably from about 0.01% to about 2%, more preferably from about 0.05% to about 1.5%, even more preferably from about 0.1% to about 1%, most preferably from about 0.2% to about 0.5%, by weight of a poly(2-oxazoline-co-ethyleneimine)-epichlorohydrin copolymer of the invention or a thermally-crosslinkable hydrophilic polymeric material of the invention.

In another preferred embodiment, a method of the invention can further comprise, before the step of heating, the steps of: contacting at room temperature the contact lens (preferably hydrogel contact lens, more preferably silicone hydrogel contact lens) with an aqueous solution of the thermally-crosslinkable hydrophilic polymeric material to form a top layer (i.e., an LbL coating) of the poly(2-oxazoline-co-ethyleneimine)-epichlorohydrin copolymer or the thermally-crosslinkable hydrophilic polymeric material on the surface of the contact lens, immersing the contact lens with the top layer of the thermally-crosslinkable hydrophilic polymeric material in a packaging solution in a lens package; sealing the lens package; and autoclaving the lens package with the contact lens therein to form a crosslinked hydrophilic coating on the contact lens.

A contact lens (preferably a hydrogel contact lens, more preferably a silicone hydrogel contact lens) obtained according to a method of the invention has a surface hydrophilicity/wettability characterized by having an averaged water contact angle of preferably about 90 degrees or less, more preferably about 80 degrees or less, even more preferably about 70 degrees or less, most preferably about 60 degrees or less.

A silicone hydrogel contact lens obtained according to a method of the invention has one property selected from the group consisting of: an oxygen permeability of at least about 40 barrers, preferably at least about 50 barrers, more preferably at least about 60 barrers, even more preferably at least about 70 barrers; an elastic modulus of about 1.5 MPa or less, preferably about 1.2 MPa or less, more preferably about 1.0 or less, even more preferably from about 0.3 MPa to about 1.0 MPa; a water content of from about 15% to about 70%, preferably from about 20% to about 65%, more preferably from about 25% to about 60%, even more preferably from about 30% to about 55% by weight when fully hydrated; a coating durability characterized by surviving a digital rubbing test and combination thereof; and combinations thereof.

The water content of a silicone hydrogel contact lens can be measured according to Bulk Technique as disclosed in U.S. Pat. No. 5,849,811.

The intrinsic "oxygen permeability", Dk, of a material is the rate at which oxygen will pass through a material. As used in this application, the term "oxygen permeability (Dk)" in reference to a hydrogel (silicone or non-silicone) or a contact lens means a measured oxygen permeability (Dk) which is corrected for the surface resistance to oxygen flux caused by the boundary layer effect according to the procedures described in Example 1 of 2012/0026457 A1 (herein incorporated by reference in its entirety). Oxygen permeability is conventionally expressed in units of barrers, where "barrer" is defined as [(cm$^3$ oxygen)(mm)/(cm$^2$)(sec)(mm Hg)]×10$^{-9}$.

The "oxygen transmissibility", Dk/t, of a lens or material is the rate at which oxygen will pass through a specific lens or material with an average thickness of t [in units of mm] over the area being measured. Oxygen transmissibility is conventionally expressed in units of barrers/mm, where "barrers/mm" is defined as [(cm$^3$ oxygen)/(cm$^2$)(sec)(mm Hg)]×10$^9$.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. A poly(2-oxazoline-co-ethyleneimine)-epichlorohydrin copolymer, comprising:
   (1) N-acyl-iminoethylene monomeric units in an amount (designated as M1) of from about 2% to about 95% by mole, wherein the N-acyl-iminoethylene monomeric units have a formula of

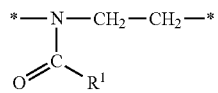

in which R$^1$ is
   (a) a monovalent radical R$^{1a}$ which is hydrogen, methyl, ethyl, propyl, isopropyl, N-pyrrolidonyl-C$_1$-C$_4$ alkyl, or a monovalent radical of -alk-(OC$_2$H$_4$)$_{m3}$—OR" in which alk is C$_1$-C$_6$ alkyl diradical, R" is C$_1$-C$_4$ alkyl, and m3 is an integer from 1 to 10, or
   (b) a monovalent radical R$^{1b}$ which is C$_4$-C$_{18}$ alkyl, C$_1$-C$_4$ alkyl-substituted phenyl, C$_1$-C$_4$-alkoxy-substituted phenyl, or C$_6$-C$_{18}$ aryl radical;

(2) azetidinium monomeric units in an amount (designated as M2) of from about 0.5% to about 95% by mole, wherein the azetidinium monomeric units have a formula of

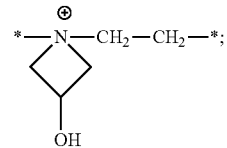

(3) ethyleneimine monomeric units in an amount (designated as M3) of from 0 to about 60% by mole, wherein the ethyleneimine monomeric units have a formula of *—NH—CH$_2$—CH$_2$—*; and
   (4) crosslink units in an amount (designated as M4) of from 0 to about 5% by mole, wherein the crosslink units have a formula of

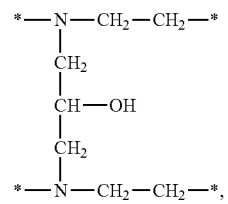

provided that (M1+M2+M3+M4) is about 100%.

2. The poly(2-oxazoline-co-ethyleneimine)-epichlorohydrin copolymer according to invention 1, wherein the poly(2-oxazoline-co-ethyleneimine)-epichlorohydrin copolymer comprises hydrophilic N-acyl-iminoethylene monomeric units of formula

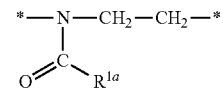

in which R$^{1a}$ is hydrogen, methyl, ethyl, propyl, isopropyl, N-pyrrolidonyl-C$_1$-C$_4$ alkyl, or a monovalent radical of -alk-(OC$_2$H$_4$)$_3$—OR" in which alk is C$_1$-C$_6$ alkyl diradical, R" is C$_1$-C$_4$ alkyl, (preferably methyl), and m3 is an integer from 1 to 10 (preferably 1 to 5).

3. The poly(2-oxazoline-co-ethyleneimine)-epichlorohydrin copolymer according to invention 1 or 2, wherein R" is methyl).

4. The poly(2-oxazoline-co-ethyleneimine)-epichlorohydrin copolymer according to invention 1, 2 or 3, wherein m3 is an integer from 1 to 5.

5. The poly(2-oxazoline-co-ethyleneimine)-epichlorohydrin copolymer according to invention 1, wherein the poly(2-oxazoline-co-ethyleneimine)-epichlorohydrin copolymer comprises hydrophobic N-acyl-iminoethylene monomeric units of formula

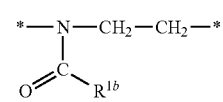

in which $R^{1b}$ is $C_6$-$C_{18}$ alkyl, $C_1$-$C_4$ alkyl-substituted phenyl, $C_1$-$C_4$-alkoxy-substituted phenyl, or $C_6$-$C_{18}$ aryl radical.

6. The poly(2-oxazoline-co-ethyleneimine)-epichlorohydrin copolymer according to invention 1, wherein the poly(2-oxazoline-co-ethyleneimine)-epichlorohydrin copolymer comprises: hydrophobic N-acyl-iminoethylene monomeric units of formula

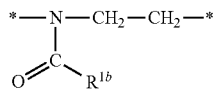

in which $R^{1b}$ is $C_6$-$C_{18}$ alkyl, $C_1$-$C_4$ alkyl-substituted phenyl, $C_1$-$C_4$-alkoxy-substituted phenyl, or $C_6$-$C_{18}$ aryl radical; and hydrophilic N-acyl-iminoethylene monomeric units of formula

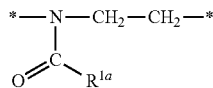

in which $R^{1a}$ is hydrogen, methyl, ethyl, propyl, isopropyl, N-pyrrolidonyl-$C_1$-$C_4$ alkyl, or a monovalent radical of -alk-$(OC_2H_4)_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)).

7. The poly(2-oxazoline-co-ethyleneimine)-epichlorohydrin copolymer according to any one of inventions 1 to 6, wherein the poly(2-oxazoline-co-ethyleneimine)-epichlorohydrin copolymer comprises: (1) from about 10% to about 85%, preferably from about 20% to about 75%, even more preferably from about 30% to about 65%, by mole of N-acyl-iminoethylene monomeric units; (2) from about 2.5% to about 75%, preferably from about 5% to about 75%, even more preferably from about 10% to about 60%, by mole of azetidinium monomeric units; (3) from 0% to about 60%, preferably from 0% to about 30%, even more preferably from 0 to about 10%, by mole of ethyleneimine monomeric units; and (4) from 0 to about 5%, preferably from 0 to about 2.5%, even more preferably from 0 to about 1%, by mole of crosslink units.

8. The poly(2-oxazoline-co-ethyleneimine)-epichlorohydrin copolymer of invention 7, wherein the poly(2-oxazoline-co-ethyleneimine)-epichlorohydrin copolymer comprises from about 20% to about 75%, even more preferably from about 30% to about 65%, by mole of N-acyl-iminoethylene monomeric units.

9. The poly(2-oxazoline-co-ethyleneimine)-epichlorohydrin copolymer of invention 7 or 8, wherein the poly(2-oxazoline-co-ethyleneimine)-epichlorohydrin copolymer comprises from about 5% to about 75%, even more preferably from about 10% to about 60%, by mole of azetidinium monomeric units.

10. The poly(2-oxazoline-co-ethyleneimine)-epichlorohydrin copolymer of invention 7, 8 or 9, wherein the poly(2-oxazoline-co-ethyleneimine)-epichlorohydrin copolymer comprises from 0% to about 30%, even more preferably from 0 to about 10%, by mole of ethyleneimine monomeric units; and (4) from 0 to about 5%, preferably from 0 to about 2.5%, even more preferably from 0 to about 1%, by mole of crosslink units.

11. The poly(2-oxazoline-co-ethyleneimine)-epichlorohydrin copolymer according to any one of inventions 7 to 10, wherein the poly(2-oxazoline-co-ethyleneimine)-epichlorohydrin copolymer comprises from 0 to about 2.5%, even more preferably from 0 to about 1%, by mole of crosslink units.

12. The poly(2-oxazoline-co-ethyleneimine)-epichlorohydrin copolymer of any one of inventions 1 to 11, having a weight average molecular weight Mw of at least about 500 Daltons, preferably from about 1,000 to about 5,000,000 Daltons, more preferably from about 5,000 to about 2,000,000 Daltons, even more preferably from about 10,000 to about 1,000,000 Daltons.

13. A water-soluble and thermally crosslinkable hydrophilic polymeric material, comprising: azetidnium groups; from about 5% to about 95% by weight of first polymer chains derived from a poly(2-oxazoline-co-ethyleneimine)-epichlorohydrin copolymer of any one of inventions 1 to 12; and from about 5% to about 95% by weight of hydrophilic moieties or second polymer chains derived from at least one hydrophilicity-enhancing agent having at least one reactive functional group selected from the group consisting of primary amino group, secondary amino group, carboxyl group, thiol group, and combination thereof.

14. The water-soluble and thermally crosslinkable hydrophilic polymeric material of invention 13, comprising from about 10% to about 90%, more preferably from about 15% to about 85%, by weight of the first polymer chains.

15. The water-soluble and thermally crosslinkable hydrophilic polymeric material of invention 13 or 14, comprising from about 10% to about 90%, even more preferably from about 15% to about 85%, by weight of the hydrophilic moieties or the second polymer chains.

16. The water-soluble and thermally crosslinkable hydrophilic polymeric material according to any one of inventions 13 to 15, wherein the hydrophilicity-enhancing polymeric agent is a hydrophilic polymers having one or more amino, carboxyl and/or thiol groups, wherein the content of the amino, carboxyl and/or thiol groups in the hydrophilic polymers as the hydrophilicity-enhancing agent is less than about 40%, preferably less than about 30%, more preferably less than about 20%, even more preferably less than about 10%, by weight based on the total weight of the hydrophilic polymer.

17. The water-soluble and thermally crosslinkable hydrophilic polymeric material of invention 16, wherein the hydrophilic polymer as the hydrophilicity-enhancing agent is: PEG-$NH_2$; PEG-SH; PEG-COOH; $H_2$N-PEG-$NH_2$; HOOC-PEG-COOH; HS-PEG-SH; $H_2$N-PEG-COOH; HOOC-PEG-SH; $H_2$N-PEG-SH; multi-arm PEG with one or more amino, carboxyl or thiol groups; PEG dendrimers with one or more amino, carboxyl or thiol groups; a diamino-, dicarboxyl-, monoamino- or monocarboxyl-terminated homo- or co-polymer of a non-reactive hydrophilic vinylic monomer; a copolymer which is a polymerization product of a composition comprising (1) about 60% by weight or less, preferably from about 0.1% to about 30%, more preferably from about 0.5% to about 20%, even more preferably from about 1% to about 15%, by weight of at least one reactive vinylic monomer and (2) at least one non-reactive hydrophilic vinylic monomer; or combinations thereof, wherein PEG is a polyethylene glycol segment.

18. The water-soluble and thermally crosslinkable hydrophilic polymeric material of invention 17, wherein the reactive vinylic monomer is selected from the group consisting of amino-$C_1$-$C_6$ alkyl (meth)acrylate, $C_1$-$C_6$ alkylamino-$C_1$-$C_6$ alkyl (meth)acrylate, allylamine, vinylamine, amino-$C_1$-$C_6$ alkyl (meth)acrylamide, $C_1$-$C_6$ alkylamino-$C_1$-$C_6$ alkyl (meth)acrylamide, acrylic acid, $C_1$-$C_4$ alkylacrylic acid, N,N-2-acrylamidoglycolic acid, beta-methyl-acrylic acid, alpha-phenyl acrylic acid, beta-acryloxy propionic acid, sorbic acid, angelic acid, cinnamic acid, 1-carboxy-4-phenyl butadiene-1,3, itaconic acid, citraconic acid, mesaconic acid, glutaconic acid, aconitic acid, maleic acid, fumaric acid, tricarboxy ethylene, and combinations thereof, wherein the non-reactive vinylic monomer is selected from the group consisting of acrylamide, methacrylamide, N,N-dimethylacrylamide, N,N-dimethylmethacrylamide, N-vinylpyrrolidone, N,N-dimethylaminoethylmethacrylate, N,N-dimethylaminoethylacrylate, N,N-dimethylaminopropylmethacrylamide, N,N-dimethylaminopropylacrylamide, glycerol methacrylate, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, hydroxypropyl (meth)acrylate, a phosphorylcholine-containing vinylic monomer, $C_1$-$C_4$-alkoxy polyethylene glycol (meth)acrylate having a weight average molecular weight of up to 1500 Daltons, N-vinyl formamide, N-vinyl acetamide, N-vinyl isopropylamide, N-vinyl-N-methyl acetamide, allyl alcohol, vinyl alcohol (hydrolyzed form of vinyl acetate in the copolymer), and combinations thereof.

19. The water-soluble and thermally crosslinkable hydrophilic polymeric material of invention 18, wherein the hydrophilic polymer as the hydrophilicity-enhancing agent is: PEG-$NH_2$; PEG-SH; PEG-COOH; $H_2$N-PEG-$NH_2$; HOOC-PEG-COOH; HS-PEG-SH; $H_2$N-PEG-COOH; HOOC-PEG-SH; $H_2$N-PEG-SH; multi-arm PEG with one or more amino, carboxyl or thiol groups; PEG dendrimers with one or more amino, carboxyl or thiol groups; a monoamino-, monocarboxyl-, diamino- or dicarboxyl-terminated homo- or copolymer of a non-reactive hydrophilic vinylic monomer selected from the group consisting of acrylamide, N,N-dimethylacrylamide, N-vinylpyrrolidone, N-vinyl-N-methyl acetamide, glycerol (meth)acrylate, hydroxyethyl (meth)acrylate, N-hydroxyethyl (meth)acrylamide, (meth)acryloyloxyethyl phosphorylcholine, $C_1$-$C_4$-alkoxy polyethylene glycol (meth)acrylate having a weight average molecular weight of up to 400 Daltons, vinyl alcohol, N-methyl-3-methylene-2-pyrrolidone, 1-methyl-5-methylene-2-pyrrolidone, 5-methyl-3-methylene-2-pyrrolidone, N,N-dimethylaminoethyl (meth)acrylate, N,N-dimethylaminopropyl (metha)crylamide, and combination thereof; a copolymer which is a polymerization product of a composition comprising (1) from about 0.1% to about 30%, preferably from about 0.5% to about 20%, more preferably from about 1% to about 15%, by weight of (meth)acrylic acid, allylamine and/or amino-$C_1$-$C_4$ alkyl (meth)acrylate, and (2) at least one non-reactive hydrophilic vinylic monomer selected from the group consisting of acrylamide, N,N-dimethylacrylamide, N-vinylpyrrolidone, N-vinyl-N-methyl acetamide, glycerol (meth)acrylate, hydroxyethyl (meth)acrylate, N-hydroxyethyl (meth)acrylamide, (meth)acryloyloxyethyl phosphorylcholine, $C_1$-$C_4$-alkoxy polyethylene glycol (meth)acrylate having a weight average molecular weight of up to 400 Daltons, vinyl alcohol, and combination thereof.

20. The water-soluble and thermally crosslinkable hydrophilic polymeric material of invention 18, wherein the hydrophilic polymer as the hydrophilicity-enhancing agent is an amino- or carboxyl-containing polysaccharide, hyaluronic acid, chondroitin sulfate, and combinations thereof.

21. The water-soluble and thermally crosslinkable hydrophilic polymeric material of invention 16, wherein the hydrophilicity-enhancing agent is: amino-, carboxyl- or thiol-containing monosaccharides; amino-, carboxyl- or thiol-containing disaccharides; and amino-, carboxyl- or thiol-containing oligosaccharides.

22. A method for producing coated contact lenses each having a crosslinked hydrophilic coating thereon comprises the steps of:
(a) obtaining a contact lens and a poly(2-oxazoline-co-ethyleneimine)-epichlorohydrin copolymer of any one of inventions 1 to 12, wherein the contact lens comprises, on and/or near the surface of the contact lens, reactive functional groups selected from the group consisting of primary amino groups, secondary amino groups, carboxyl groups, and combinations thereof; and
(b) heating the contact lens in an aqueous solution in the presence of the poly(2-oxazoline-co-ethyleneimine)-epichlorohydrin copolymer to and at a temperature from about 40° C. to about 140° C. for a period of time sufficient to covalently attach the poly(2-oxazoline-co-ethyleneimine)-epichlorohydrin copolymer onto the surface of the contact lens through covalent linkages each formed between one azetidinium group of the poly(2-oxazoline-co-ethyleneimine)-epichlorohydrin copolymer and one of the reactive functional groups on and/or near the surface of the contact lens, thereby forming a crosslinked hydrophilic coating on the contact lens.

23. The method of invention 22, wherein the contact lenses are silicone hydrogel contact lenses.

24. A method for producing coated contact lenses each having a crosslinked hydrophilic coating thereon comprises the steps of:
(a) obtaining a contact lens;
(b) applying a layer of a poly(2-oxazoline-co-ethyleneimine)-epichlorohydrin copolymer of invention 5 or 6 to form an anchoring coating on the silicone hydrogel contact lens, wherein the poly(2-oxazoline-co-ethyleneimine)-epichlorohydrin copolymer comprises hydrophobic N-acyl-iminoethylene monomeric units; and
(c) heating the contact lens having the anchoring coating thereon in an aqueous solution to and at a temperature from about 40° C. to about 140° C. in the presence of a water-soluble hydrophilic polymer having reactive functional groups selected from the group consisting of primary amino groups, secondary amino groups, carboxyl groups, thiol groups, and combinations thereof, for a period of time sufficient to covalently attach the hydrophilic polymer onto the surface of the contact lens through covalent linkages each formed between one azetidinium group of the anchoring coating and one of the reactive functional groups of the hydrophilic polymer, thereby forming a crosslinked hydrophilic coating on the contact lens.

25. The method of invention 24, wherein the contact lenses are silicone hydrogel contact lenses.

26. The method of invention 24 or 25, wherein the step (b) is carried out by dipping the contact lens into a coating solution of the poly(2-oxazoline-co-ethyleneimine)-epichlorohydrin copolymer or by spraying the contact lens with the coating solution.

27. The method according to any one of inventions 24 to 26, wherein the coating of the poly(2-oxazoline-co-ethyleneimine)-epichlorohydrin copolymer is prepared by dissolving the poly(2-oxazoline-co-ethyleneimine)-epichlorohydrin copolymer in an organic solvent, a mixture of two or more organic solvents, a mixture of water with one or more organic solvent.

28. A method for producing coated contact lenses each having a crosslinked hydrophilic coating thereon comprises the steps of:
   (a) obtaining a contact lens and a water-soluble and thermally-crosslinkable hydrophilic polymeric material of any one of claims 7 to 13, wherein the contact lens comprises, on and/or near the surface of the contact lens, reactive functional groups selected from the group consisting of primary amino groups, secondary amino groups, carboxyl groups, and combinations thereof; and
   (b) heating the contact lens in an aqueous solution in the presence of the water-soluble and thermally-crosslinkable hydrophilic polymeric material to and at a temperature from about 40° C. to about 140° C. for a period of time sufficient to covalently attach the hydrophilic polymeric material onto the surface of the contact lens through covalent linkages each formed between one azetidinium group of the poly(2-oxazoline-co-ethyleneimine)-epichlorohydrin copolymer and one of the reactive functional groups on and/or near the surface of the contact lens, thereby forming a crosslinked hydrophilic coating on the contact lens.

29. The method of any one of inventions 22 to 28, wherein the step of heating is performed in a lens package containing the contact lens immersed in a packaging solution, more preferably by autoclaving the contact lens immersed in a packaging solution in a sealed lens package at a temperature of from about 118° C. to about 125° C. for approximately 20-90 minutes to form the crosslinked hydrophilic coating on the contact lens, wherein the packaging solution comprises at least one buffering agent in an amount sufficient to maintain a pH of from about 6.0 to about 8.5 and has a tonicity of from about 200 to about 450 milliosmol (mOsm), preferably from about 250 to about 350 mOsm and a viscosity of from about 1 centipoise to about 20 centipoises, preferably from about 1.5 centipoises to about 10 centipoises, more preferably from about 2 centipoises to about 5 centipoises, at 25° C.

30. The method of any one of inventions 22 to 29, wherein the contact lens is made by polymerizing a lens formulation comprising at least one reactive vinylic monomer selected from the group consisting of: amino-$C_1$-$C_6$ alkyl (meth)acrylate, $C_1$-$C_6$ alkylamino-$C_1$-$C_6$ alkyl (meth)acrylate, allylamine, vinylamine, amino-$C_1$-$C_6$ alkyl (meth)acrylamide, $C_1$-$C_6$ alkylamino-$C_1$-$C_6$ alkyl (meth)acrylamide, acrylic acid, $C_1$-$C_4$ alkylacrylic acid, N,N-2-acrylamidoglycolic acid, beta methyl-acrylic acid, alpha-phenyl acrylic acid, beta-acryloxy propionic acid, sorbic acid, angelic acid, cinnamic acid, 1-carboxy-4-phenyl butadiene-1,3, itaconic acid, citraconic acid, mesaconic acid, glutaconic acid, aconitic acid, maleic acid, fumaric acid, tricarboxy ethylene, and combinations thereof.

31. The method according to any one of inventions 22 to 29, wherein the contact lens is made by polymerizing a lens formulation comprising at least one reactive vinylic monomer selected from the group consisting of: amino-$C_1$-$C_6$ alkyl (meth)acrylate, $C_1$-$C_6$ alkylamino-$C_1$-$C_6$ alkyl (meth)acrylate, allylamine, amino-$C_1$-$C_6$ alkyl (meth)acrylamide, $C_1$-$C_6$ alkylamino-$C_1$-$C_6$ alkyl (meth)acrylamide, acrylic acid, $C_1$-$C_6$ alkylacrylic acid, and combinations thereof.

32. The method of invention 30 or 31, wherein the lens formulation comprises from about 0.1% to about 10%, more preferably from about 0.25% to about 7%, even more preferably from about 0.5% to about 5%, most preferably from about 0.75% to about 3%, by weight of the reactive vinylic monomer.

33. The method of any one of inventions 22-32, wherein the contact lens comprises a reactive base coating including amino and/or carboxyl groups.

34. The method of invention 33, wherein the reactive base coating comprises at least one layer of a reactive polymer having pendant amino groups and/or carboxyl groups and is obtained by contacting the silicone hydrogel contact lens with a solution of the reactive polymer, wherein the reactive polymer is: a homopolymer of amino-$C_1$ to $C_4$ alkyl (meth)acrylamide, amino-$C_1$ to $C_4$ alkyl (meth)acrylate, $C_1$ to $C_4$ alkylamino-$C_1$ to $C_4$ alkyl (meth)acrylamide, $C_1$ to $C_4$ alkylamino-$C_1$ to $C_4$ alkyl (meth)acrylate, allylamine, or vinylamine; polyethyleneimine; a polyvinylalcohol with pendant amino groups; a linear or branched polyacrylic acid; a homopolymer of $C_1$ to $C_4$ alkylacrylic acid; a copolymer of amino-$C_1$ to $C_4$ alkyl (meth)acrylamide, amino-$C_1$ to $C_4$ alkyl (meth)acrylate, $C_1$ to $C_4$ alkylamino-$C_1$ to $C_4$ alkyl (meth)acrylamide, $C_1$ to $C_4$ alkylamino-$C_1$ to $C_4$ alkyl (meth)acrylate, acrylic acid, $C_1$ to $C_4$ alkylacrylic acid, maleic acid, and/or fumaric acid, with at least one non-reactive hydrophilic vinylic monomer (preferably selected from the group consisting of acrylamide, N,N-dimethyl (meth)acrylamide, N-vinylpyrrolidone, glycerol methacrylate, N,N-2-acrylamidoglycolic acid, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, 1-n-butyl-3-methylene-2-pyrrolidone, 1-tert-butyl-3-methylene-2-pyrrolidone, 2-hydroxyethyl (meth)acrylate, hydroxypropyl (meth)acrylate, (meth)acryloyloxyethyl phosphorylcholine, $C_1$-$C_4$-alkoxy polyethylene glycol (meth)acrylate having a weight average molecular weight of up to 1500 Daltons, N-vinyl formamide, N-vinyl acetamide, N-vinyl isopropylamide, N-vinyl-N-methyl acetamide, allyl alcohol, vinyl alcohol (hydrolyzed form of vinyl acetate in the copolymer), and combination thereof); a carboxyl-containing cellulose; hyaluronate; chondroitin sulfate; poly(glutamic acid); poly(aspartic acid); or combinations thereof.

35. The method of invention 34, wherein the reactive polymer for forming a base coating is polyacrylic acid, polymethacrylic acid, poly[(meth)acrylic acid-co-acrylamide], poly[(meth)acrylic acid-co-vinylpyrrolidone], hydrolyzed poly[(meth)acrylic acid-co-vinylacetate], polyethyleneimine, polyallylamine homo- or copolymer, polyvinylamine homo- or copolymer, or combinations thereof.

36. The method of invention 34 or 35, wherein the reactive polymer is dissolved in a mixture of water and one or more organic solvents, an organic solvent, or a mixture of one or more organic solvent.

37. The method of invention 33, wherein the reactive base coating on the contact lens is obtained by polymerizing at least one amino-containing or carboxyl-containing vinylic monomer under the effect of a plasma.

38. A contact lens product obtained according to the method of any one of inventions 22 to 37.

39. The contact lens of invention 38, wherein the contact lens is a silicone hydrogel contact lens that has at least one property selected from the group consisting of: an oxygen permeability of at least about 40 barrers, preferably at least about 50 barrers, more preferably at least about 60 barrers, even more preferably at least about 70 barrers; an elastic modulus of about 1.5 MPa or less, preferably about 1.2 MPa or less, more preferably about 1.0 or less, even more preferably from about 0.2 MPa to about 1.0 MPa; an Ionoflux Diffusion Coefficient, D, of, at least about $1.5 \times 10^{-6}$ mm$^2$/min, preferably at least about $2.6 \times 10^{-6}$ mm$^2$/min, more preferably at least about $6.4 \times 10^{-6}$ mm$^2$/min; a water content of from about 18% to about 70%, preferably from about 20% to about 60% by weight when fully hydrated; and combinations thereof.

40. The contact lens of invention 38, wherein the contact lens is a hydrogel contact lens that has at least one property selected from the group consisting of: an elastic modulus of about 1.5 MPa or less, preferably about 1.2 MPa or less, more preferably about 1.0 or less, even more preferably from about 0.2 MPa to about 1.0 MPa; and a water content of from about 18% to about 70%, preferably from about 20% to about 60% by weight when fully hydrated; and combinations thereof.

Example 1

500 mL of DI water is added to a 3 liter round bottom flask. The flask has at least 3 necks. The center neck contains a glass stir rod and paddle for stirring the formation. Another neck contains a reflux condenser cooled to about 2° C. 100 grams of poly(2-ethyl-2-oxazoline) (PEOZO 50 kDa) is added to the flask over about 15 minutes while stirring at about 150 rpm. After addition is complete, stirring continues until the PEOZO is completely dissolved. 1000 mL of 10% HCl is added to the PEOZO solution over about 15 minutes with stirring. The stir rate is increased to about 200 rpm. A thermocouple is added to the third neck to monitor temperature. A heating mantle is used to heat the solution up to the boiling point. This temperature of about 102° C. is maintained for a specified period of time (1 to 7 hours). After the specified time, the heating mantle is removed and the solution is allowed to cool. When the solution cools to less than 70° C., neutralization can begin. 5N NaOH is added to the solution using an addition funnel with stirring over at least 30 minutes. Addition stops when the pH reaches between 8 and 10. The solution is allowed to cool to room temperature. The solution is filtered through 1 um filter paper.

Example 2

The solution from Example 1 is purified by ultrafiltration using 3 kDa regenerated cellulose membranes from Millipore. The solution is concentrated to about 2 liters, if necessary, and about 40 liters of water is collected as permeate through the filters. During the purification pH should be adjusted to maintain a pH between 9 and 11. The conductivity of the permeate should also be less than 10 μS/cm at the end. Some of the sample is then isolated by freeze-drying and used for $^1$H NMR analysis. NMR is useful to determine purity and the percentage of amide hydrolysis. Table 1 below shows the % amide hydrolyzed as function of reaction time as determined by $^1$H NMR.

TABLE 1

| | Sample | | | |
|---|---|---|---|---|
| | 3A | 3B | 3C | 3D |
| Reaction time (hours) | 1 | 3 | 5 | 7 |
| Amide Hydrolysis (%) | 32 | 76 | 89 | 92 |

Example 3

This example illustrates how to prepare poly(2-oxazoline-co-ethylenimine)-epichlorohydrin copolymers according to procedures similar to what described in the paper of Obokata and coworkers (*J. Appl. Polym. Sci.* 2005, 97, 2249, herein incorporated by reference in its entirety) and as illustrated in the following scheme.

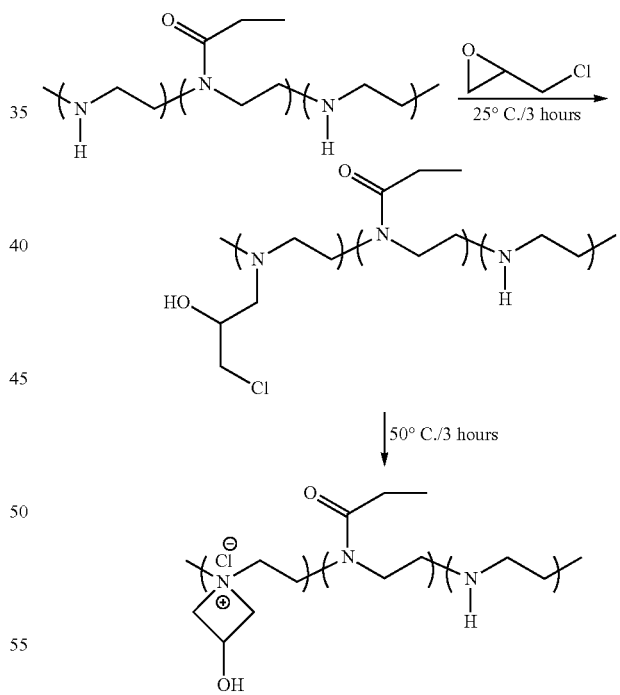

A hydrolyzed polyoxazoline prepared in Example 2 is dissolved in an polar solvent such as acetonitrile, tetrahydrofuran, 1,4-dioxane, water or a combination of any of the two followed by adding desire amount of epichlorhydrin from 5% to 100% according to the total amine content, preferred from 30% to 70%. The mixture is stirred in a desired temperature range from 0° C. to 70° C., preferred 20° C. to 30° C. for 1 to 5 hours depending upon the applied reaction temperature. The most desired combination according to the current experimental results is 25° C. for 3 hours in which the epichlorhydrin is fully reacted to secondary amine without having side reaction or further ring close reaction as described in below.

After the epichlorhydrin is fully consumed, the reaction temperature is elevated to 40-60° C. and maintained at that temperature for about 2 hours to form the azetidinium group. If it is desirable to have a slightly branched final product, the reaction can be extended at 60° C. which allows the residual secondary amine groups to react with the newly formed azetidinum groups until the target architecture is achieved.

If needed, the reaction can be stopped by adding sulfuric acid and reducing the pH to about 3.

After the reaction is completed, the final product can be purified with ultrafiltration followed with a pH adjustment to 3 and then storage at frozen temperature until further usage.

What is claimed is:

1. A water-soluble and thermally crosslinkable hydrophilic polymeric material, comprising:
   (a) azetidnium groups;
   (b) from about 5% to about 95% by weight of first polymer chains derived from a poly(2-oxazoline-co-ethyleneimine)-epichlorohydrin copolymer which comprises
      (1) N-acyl-iminoethylene monomeric units in an amount (designated as M1) of from about 2% to about 95% by mole, wherein the N-acyl-iminoethylene monomeric units have a formula of

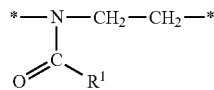

in which $R^1$ is a monovalent radical $R^{1a}$ which is hydrogen, methyl, ethyl, propyl, isopropyl, N-pyrrolidonyl-$C_1$-$C_4$ alkyl, or a monovalent radical of -alk-$(OC_2H_4)_{m3}$—OR" in which alk is $C_1$-$C_6$ alkyl diradical, R" is $C_1$-$C_4$ alkyl, and m3 is an integer from 1 to 10,
      (2) azetidinium monomeric units in an amount (designated as M2) of from about 0.5% to about 95% by mole, wherein the azetidinium monomeric units have a formula of

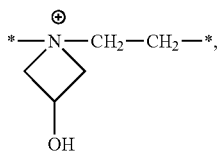

(3) ethyleneimine monomeric units in an amount (designated as M3) of from 0 to about 60% by mole, wherein the ethyleneimine monomeric units have a formula of *—NH—$CH_2$—$CH_2$—*, and
      (4) crosslink units in an amount (designated as M4) of from 0 to about 5% by mole, wherein the crosslink units have a formula of

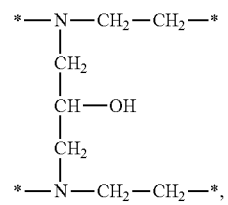

provided that (M1+M2+M3+M4) is about 100%; and
   (c) from about 5% to about 95% by weight of hydrophilic moieties or second polymer chains derived from at least one hydrophilicity-enhancing agent having at least one reactive functional group selected from the group consisting of primary amino group, secondary amino group, carboxyl group, thiol group, and combination thereof.

2. The water-soluble and thermally crosslinkable hydrophilic polymeric material of claim 1, wherein the hydrophilicity-enhancing polymeric agent is a hydrophilic polymers having one or more amino, carboxyl and/or thiol groups, wherein the content of the amino, carboxyl and/or thiol groups in the hydrophilic polymer as the hydrophilicity-enhancing agent is less than about 40% by weight based on the total weight of the hydrophilic polymer.

3. The water-soluble and thermally crosslinkable hydrophilic polymeric material of claim 2, wherein the hydrophilic polymer as the hydrophilicity-enhancing agent is: PEG-$NH_2$; PEG-SH; PEG-COOH; $H_2$N-PEG-$NH_2$; HOOC-PEG-COOH; HS-PEG-SH; $H_2$N-PEG-COOH; HOOC-PEG-SH; $H_2$N-PEG-SH; multi-arm PEG with one or more amino, carboxyl or thiol groups; PEG dendrimers with one or more amino, carboxyl or thiol groups; a diamino-, dicarboxyl-, monoamino- or monocarboxyl-terminated homo- or co-polymer of a non-reactive hydrophilic vinylic monomer; a copolymer which is a polymerization product of a composition comprising (1) about 60% by weight or less, preferably from about 0.1% to about 30%, more preferably from about 0.5% to about 20%, even more preferably from about 1% to about 15%, by weight of at least one reactive vinylic monomer and (2) at least one non-reactive hydrophilic vinylic monomer; or combinations thereof, wherein PEG is a polyethylene glycol segment.

4. The water-soluble and thermally crosslinkable hydrophilic polymeric material of claim 3, wherein the reactive vinylic monomer is selected from the group consisting of amino-$C_1$-$C_6$ alkyl (meth)acrylate, $C_1$-$C_6$ alkylamino-$C_1$-$C_6$ alkyl (meth)acrylate, allylamine, vinylamine, amino-$C_1$-$C_6$ alkyl (meth)acrylamide, $C_1$-$C_6$ alkylamino-$C_1$-$C_6$ alkyl (meth)acrylamide, acrylic acid, $C_1$-$C_4$ alkylacrylic acid, N,N-2-acrylamidoglycolic acid, beta-methyl-acrylic acid, alpha-phenyl acrylic acid, beta-acryloxy propionic acid, sorbic acid, angelic acid, cinnamic acid, 1-carboxy-4-phenyl butadiene-1,3, itaconic acid, citraconic acid, mesaconic acid, glutaconic acid, aconitic acid, maleic acid, fumaric acid, tricarboxy ethylene, and combinations thereof,
   wherein the non-reactive vinylic monomer is selected from the group consisting of acrylamide, methacrylamide, N,N-dimethylacrylamide, N,N-dimethylmethacrylamide, N-vinylpyrrolidone, N,N-dimethylaminoethylmethacrylate, N,N-dimethylaminoethylacrylate, N,N-dimethylaminopropylmethacrylamide, N,N-dimethylaminopropylacrylamide, glycerol methacrylate, 3-acryloylamino-1-propanol, N-hydroxyethyl acrylamide, N-[tris(hydroxymethyl)methyl]acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, hydroxypropyl (meth)acrylate, a phosphorylcholine-containing vinylic monomer, $C_1$-$C_4$-alkoxy polyethylene glycol (meth)acrylate having a weight average molecular weight of up to 1500 Daltons, N-vinyl formamide, N-vinyl acetamide, N-vinyl isopropylamide, N-vinyl-N-methyl acetamide, allyl alcohol, vinyl alcohol (hydrolyzed form of vinyl acetate in the copolymer), and combinations thereof.

5. The water-soluble and thermally crosslinkable hydrophilic polymeric material of claim 2, wherein the hydrophilic polymer as the hydrophilicity-enhancing agent is: PEG-$NH_2$; PEG-SH; PEG-COOH; $H_2$N-PEG-$NH_2$; HOOC-PEG-COOH; HS-PEG-SH; $H_2$N-PEG-COOH; HOOC-PEG-SH; $H_2$N-PEG-SH; multi-arm PEG with one or more amino, carboxyl or thiol groups; PEG dendrimers with one or more amino, carboxyl or thiol groups; a monoamino-, monocarboxyl-, diamino- or dicarboxyl-terminated homo- or copolymer of a non-reactive hydrophilic vinylic monomer selected from the group consisting of acryamide, N,N-dimethylacrylamide, N-vinylpyrrolidone, N-vinyl-N-methyl acetamide, glycerol (meth)acrylate, hydroxyethyl (meth)acrylate, N-hydroxyethyl (meth)acrylamide, (meth)acryloyloxyethyl phosphorylcholine, $C_1$-$C_4$-alkoxy polyethylene glycol (meth)acrylate having a weight average molecular weight of up to 400 Daltons, vinyl alcohol, N-methyl-3-methylene-2-pyrrolidone, 1-methyl-5-methylene-2-pyrrolidone, 5-methyl-3-methylene-2-pyrrolidone, N,N-dimethylaminoethyl (meth)acrylate, N,N-dimethylaminopropyl (metha)crylamide, and combination thereof; a copolymer which is a polymerization product of a composition comprising (1) from about 0.1% to about 30%, preferably from about 0.5% to about 20%, more preferably from about 1% to about 15%, by weight of (meth)acrylic acid, allylamine and/or amino-$C_1$-$C_4$ alkyl (meth)acrylate, and (2) at least one non-reactive hydrophilic vinylic monomer selected from the group consisting of acryamide, N,N-dimethylacrylamide, N-vinylpyrrolidone, N-vinyl-N-methyl acetamide, glycerol (meth)acrylate, hydroxyethyl (meth)acrylate, N-hydroxyethyl (meth)acrylamide, (meth)acryloyloxyethyl phosphorylcholine, $C_1$-$C_4$-alkoxy polyethylene glycol (meth)acrylate having a weight average molecular weight of up to 400 Daltons, vinyl alcohol, and combination thereof.

6. The water-soluble and thermally crosslinkable hydrophilic polymeric material of claim 2, wherein the hydrophilic polymer as the hydrophilicity-enhancing agent is an amino- or carboxyl-containing polysaccharide, hyaluronic acid, chondroitin sulfate, and combinations thereof.

7. The water-soluble and thermally crosslinkable hydrophilic polymeric material of claim 1, wherein the hydrophilicity-enhancing agent is: amino-, carboxyl- or thiol-containing monosaccharides; amino-, carboxyl- or thiol-containing disaccharides; and amino-, carboxyl- or thiol-containing oligosaccharides.

8. A method for producing coated contact lenses each having a crosslinked hydrophilic coating thereon comprises the steps of:
(a) obtaining a contact lens, wherein the contact lens comprises, on and/or near the surface of the contact lens, reactive functional groups selected from the group consisting of primary amino groups, secondary amino groups, carboxyl groups, and combinations thereof;
(b) obtaining a water-soluble and thermally-crosslinkable hydrophilic polymeric material of claim 1; and
(c) heating the contact lens in an aqueous solution in the presence of the water-soluble and thermally-crosslinkable hydrophilic polymeric material to and at a temperature from about 40° C. to about 140° C. for a period of time sufficient to covalently attach the hydrophilic polymeric material onto the surface of the contact lens through covalent linkages each formed between one azetidinium group of the poly(2-oxazoline-co-ethyleneimine)-epichlorohydrin copolymer and one of the reactive functional groups on and/or near the surface of the contact lens, thereby forming a crosslinked hydrophilic coating on the contact lens.

9. The method of claim 8, wherein the step of heating is performed by autoclaving the contact lens immersed in a packaging solution in a sealed lens package at a temperature of from about 118° C. to about 125° C. for approximately 20-90 minutes to form the crosslinked hydrophilic coating on the contact lens, wherein the packaging solution comprises at least one buffering agent in an amount sufficient to maintain a pH of from about 6.0 to about 8.5 and has a tonicity of from about 200 to about 450 milliosmol (mOsm) and a viscosity of from about 1 centipoise to about 20 centipoises at 25° C.

10. The method of claim 8, wherein the contact lens is made by polymerizing a silicone hydrogel lens formulation comprising from about 0.1% to about 10% by weight of at least one reactive vinylic monomer selected from the group consisting of: amino-$C_1$-$C_6$ alkyl (meth)acrylate, $C_1$-$C_6$ alkylamino-$C_1$-$C_6$ alkyl (meth)acrylate, allylamine, amino-$C_1$-$C_6$ alkyl (meth)acrylamide, $C_1$-$C_6$ alkylamino-$C_1$-$C_6$ alkyl (meth)acrylamide, acrylic acid, $C_1$-$C_6$ alkylacrylic acid, and combinations thereof.

11. The method of claim 8, wherein the contact lens comprises a reactive base coating including amino and/or carboxyl groups.

12. The method of claim 11, wherein the reactive base coating comprises at least one layer of a reactive polymer having pendant amino groups and/or carboxyl groups and is obtained by contacting the contact lens with a solution of the reactive polymer, wherein the reactive polymer is: a homopolymer of amino-$C_1$ to $C_4$ alkyl (meth)acrylamide, amino-$C_1$ to $C_4$ alkyl (meth)acrylate, $C_1$ to $C_4$ alkylamino-$C_1$ to $C_4$ alkyl (meth)acrylamide, $C_1$ to $C_4$ alkylamino-$C_1$ to $C_4$ alkyl (meth)acrylate, allylamine, or vinylamine; polyethyleneimine; a polyvinylalcohol with pendant amino groups; a linear or branched polyacrylic acid; a homopolymer of $C_1$ to $C_4$ alkylacrylic acid; a copolymer of amino-$C_1$ to $C_4$ alkyl (meth)acrylamide, amino-$C_1$ to $C_4$ alkyl (meth)acrylate, $C_1$ to $C_4$ alkylamino-$C_1$ to $C_4$ alkyl (meth)acrylamide, $C_1$ to $C_4$ alkylamino-$C_1$ to $C_4$ alkyl (meth)acrylate, acrylic acid, $C_1$ to $C_4$ alkylacrylic acid, maleic acid, and/or fumaric acid, with at least one non-reactive hydrophilic vinylic monomer (preferably selected from the group consisting of acrylamide, N,N-dimethyl (meth)acrylamide, N-vinylpyrrolidone, glycerol methacrylate, N,N-2-acrylamidoglycolic acid, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, 1-n-butyl-3-methylene-2-pyrrolidone, 1-tert-butyl-3-methylene- 2-pyrrolidone, 2-hydroxyethyl (meth)acrylate, hydroxypropyl (meth)acrylate, (meth)acryloyloxyethyl phosphorylcholine, $C_1$-$C_4$-alkoxy polyethylene glycol (meth)acrylate having a weight average molecular weight of up to 1500 Daltons, N-vinyl formamide, N-vinyl acetamide, N-vinyl isopropylamide, N-vinyl-N-methyl acetamide, allyl alcohol, vinyl alcohol (hydrolyzed form of vinyl acetate in the copolymer), and combination thereof); a carboxyl-containing cellulose; hyaluronate; chondroitin sulfate; poly(glutamic acid); poly(aspartic acid); or combinations thereof.

13. The method of claim 12, wherein the reactive polymer is dissolved in a mixture of water and one or more organic solvents, an organic solvent, or a mixture of one or more organic solvents.

14. A contact lens product obtained according to the method of claim 8, wherein the contact lens is a hydrogel contact lens or a silicone hydrogel contact lens; wherein the hydrogel or silicone hydrogel contact lens has an elastic modulus of about 1.5 MPa or less and a water content of from about 18% to about 70% by weight when fully hydrated.

* * * * *